(12) United States Patent
Dionne et al.

(10) Patent No.: US 10,611,752 B2
(45) Date of Patent: Apr. 7, 2020

(54) ENANTIOSELECTIVE DESTRUCTION OF CHIRAL MOLECULES

(71) Applicant: The Board of Trustees of the Leland Stanford Junior University, Stanford, CA (US)

(72) Inventors: Jennifer Anne Dionne, Menlo Park, CA (US); Chi-Sing Ho, Stanford, CA (US); Aitzol Imanol Garcia Echarri, Gipuzkoa (ES)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 206 days.

(21) Appl. No.: 15/446,855

(22) Filed: Mar. 1, 2017

(65) Prior Publication Data

US 2017/0253538 A1    Sep. 7, 2017

Related U.S. Application Data

(60) Provisional application No. 62/302,108, filed on Mar. 1, 2016.

(51) Int. Cl.
| | | |
|---|---|---|
| *C07D 401/12* | (2006.01) | |
| *C07D 211/34* | (2006.01) | |
| *C07C 45/85* | (2006.01) | |
| *C07C 51/487* | (2006.01) | |
| *C07C 213/10* | (2006.01) | |

(52) U.S. Cl.
CPC ............ *C07D 401/12* (2013.01); *C07C 45/85* (2013.01); *C07C 51/487* (2013.01); *C07C 213/10* (2013.01); *C07D 211/34* (2013.01); *C07B 2200/07* (2013.01)

(58) Field of Classification Search
CPC ................................................ B01J 2219/1206
See application file for complete search history.

(56) References Cited

U.S. PATENT DOCUMENTS

| | | | | |
|---|---|---|---|---|
| 5,011,756 A | * | 4/1991 | Nikles ................. | G11B 7/0045 346/135.1 |
| 5,628,730 A | | 5/1997 | Shapland et al. | |

(Continued)

FOREIGN PATENT DOCUMENTS

CN         104059091        9/2011

OTHER PUBLICATIONS

Flores et al. (Journal of the American Chemical Society, 99:11, 1977, p. 3622-3625) (Year: 1977).*

(Continued)

*Primary Examiner* — Liam J Heincer
(74) *Attorney, Agent, or Firm* — Knobbe, Martens, Olson & Bear, LLP

(57) ABSTRACT

Methods and devices are disclosed for selective photo-destruction of one chiral enantiomer of a compound using nanostructures by enhancing differential absorption of circularly polarized light by the one chiral enantiomer. Methods and devices are disclosed for selective enrichment of one chiral enantiomer of a compound using nanostructures by enhancing differential absorption of circularly polarized light by the one chiral enantiomer. The nanostructures support optical frequency electric resonances and optical frequency magnetic resonances.

10 Claims, 10 Drawing Sheets

(56) References Cited

U.S. PATENT DOCUMENTS

| | | | |
|---|---|---|---|
| 6,808,603 B1* | 10/2004 | Nishino | C07B 53/00 |
| | | | 204/157.15 |
| 8,084,266 B2 | 12/2011 | Ishihara et al. | |
| 8,379,198 B2 | 2/2013 | Miller et al. | |
| 2004/0026660 A1* | 2/2004 | Vaughan-Spickers | |
| | | | C09K 19/2028 |
| | | | 252/299.01 |
| 2016/0167136 A1* | 6/2016 | Kotov | B22F 9/24 |
| | | | 420/507 |

OTHER PUBLICATIONS

Feringa et al. (Angew. Chem. Int. Ed. 1999, 38,3418-3438) (Year: 1999).*

Schellman (Circular Dichroism and Optical Rotation, Chemical Reviews, 1975, vol. 75(3), p. 323-331) (Year: 1975).*

Ahuja, S., Chiral Separation Methods for Pharmaceutical and Biotechnological Products, John Wiley & Sons; 2011.

Alizadeh, M.H. et al., Plasmonically Enhanced Chiral Optical Fields and Forces in Achiral Split Ring Resonators, ACS Photonics, vol. 2, No. 3, pp. 361-368; 2015.

Analytical / Chromatography Products, Sigma-Aldrich, 2017; http://www.sigmaaldrich.com/analytical-chromatography/analytical-chromatography-catalog.html; Original publication date unknown; Version submitted herewith downloaded on Mar. 16, 2017.

Bakker, R.M. et al., Magnetic and electric hotspots with silicon nanodimers, Nano Letters, vol. 15, No. 3, pp. 2137-2142; 2015.

Balavoine, G. et al., Preparation of chiral compounds with high optical purity by irradiation with circularly polarized light, a model reaction for the prebiotic generation of optical activity, Journal of the American Chemical Society, vol. 96, No. 16, pp. 5152-5158; 1974.

Barron, L.D., Molecular Light Scattering and Optical Activity, Cambridge University Press, $2^{nd}$ Edition, 2004.

Bohren, C.F., et al., Absorption and Scattering of Light by Small Particles, John Wiley & Sons, ebook, 2008.

Cameron, R.P. et al., Discriminatory optical force for chiral molecules, New Journal of Physics, vol. 16, 013020; 2014.

Canagier-Durand, A. et al., Mechanical separation of chiral dipoles by chiral light, New Journal of Physics, vol. 15, 123037; 2013.

Chhabra, N. et al., A review of drug isomerism and its significance, International Journal of Applied & Basic Medical Research, vol. 3, No. 1, pp. 16-18; 2013.

Choi, J.S. et al., Limitations of a superchiral field, Physical Review A, vol. 86, No. 6, 063834; 2012.

Choi, M. et al., A terahertz metamaterial with unnaturally high refractive index, Nature, vol. 470, No. 7334, pp. 369-373; 2011.

Development of New Stereoisomeric Drugs. 1992; http://www.fda.gov/Drugs/GuidanceComplianceRegulatoryInformation/Guidances/ucm122883.htm, accessed Sep. 3, 2016.

Duan, X. et al., Hydrogen-Regulated Chiral Nanoplasmonics, Nano Letters, vol. 6, No. 2, pp. 1462-1466; 2016.

Esposito, M. et al., Nanoscale 3D Chiral Plasmonic Helices with Circular Dichroism at Visible Frequencies, ACS Photonics, vol. 2, No. 1, pp. 105-114; 2014.

Fan, J.A. et al., Selfassembled plasmonic nanoparticle clusters, Science, vol. 328, No. 5982, pp. 1135-1138; 2010.

Feringa, B.L. et al., Absolute Asymmetric Synthesis: The Origin, Control, and Amplification of Chirality, Angewandte Chemie International Edition, vol. 38, No. 23, pp. 3418-3438; 1999.

Ferry, V.E. et al., Circular Dichroism in Off-Resonantly Coupled Plasmonic Nanosystems, Nano Letters, vol. 15, No. 12, pp. 8336-8341; 2015.

Garcia-Etxarri, A. et al., Strong magnetic response of submicron Silicon particles in the infrared, Optical Society of America, vol. 19, No. 6, pp. 4815-4826; 2011.

Garcia-Etxarri, A., Polarization singularities on high index nanoparticles, Cornell University Library, eprint arXiv:1601.04365; 2016.

Garcia-Etxarri, A., et al., Surface enhanced circular dichroism spectroscopy mediated by non-chiral nanoantennas, Physical Review B, vol. 87, pp. 235409; 2013.

Hayat, A. et al., Lateral chirality-sorting optical forces, Proceedings of the National Academy of Sciences USA, vol. 112, No. 43, pp. 13190-13194; 2015.

Hendry, E. et al., Ultrasensitive detection and characterization of biomolecules using superchiral fields, Nature Nanotechnology, vol. 5, pp. 783-787; 2010.

Ho, C. et al., Enhancing Enantioselective Absorption Using Dielectric Nanospheres, ACS Photonics, vol. 4, No. 2, 197-203, DOI: 10.1021/acsphotonics.6b00701; 2016.

Kagan, H.B. et al., Can circularly polarized light be used to obtain chiral compounds of high optical purity?, Journal of Molecular Evolution, vol. 4, No. 1, pp. 41-48; 1974.

Lewis, D.L. et al., Influence of environmental changes on degradation of chiral pollutants in soils, Nature, vol. 401, pp. 898-901; 1999.

Li, B. et al., Lead germanium telluride: a mechanically robust infrared high-index layer, Journal of Materials Science, vol. 46, No. 11, pp. 4000-4004; 2011.

Li, B. et al., Low-temperature dependence of midinfrared optical constants of lead-germaniumtelluride thin film, Journal of Applied Physics, vol. 91, No. 6, 3556; 2002.

Lipkin, D.M., Existence of a New Conservation Law in Electromagnetic Theory, Journal of Mathematical Physics, vol. 5, No. 5, pp. 696-700; 1964.

Lu, F. et al., Discrete Nanocubes as Plasmonic Reporters of Molecular Chirality, Nano Letters, vol. 13, No. 7, pp. 3145-3151; 2013.

Modica, P. et al., Enantiomeric Excesses Induced in Amino Acids by Ultraviolet Circularly Polarized Light Irradiation of Extraterrestrial Ice Analogs: a Possible Source of Asymmetry for Prebiotic Chemistry, The Astrophysical Journal, vol. 788, No. 1, pp. 1-11; 2014.

Nguyen, L.A. et al., Chiral drugs: an overview, International Journal of Biomedical Sciences, vol. 2, No. 2, pp. 85-100; 2006.

Rhee, H. et al., Femtosecond characterization of vibrational optical activity of chiral molecules, Nature, vol. 458, pp. 310-313; 2009.

Rodriguez-Fortuno, F.J. et al., Lateral forces on circularly polarizable particles near a surface, Nature Communications, vol. 6, 8799; 2015.

Sainidou, R. et al., Plasmon guided modes in nanoparticle metamaterials, Optical Society of America, vol. 16, No. 7, pp. 4499-4506; 2008.

Schaferling, M. et al., Helical Plasmonic Nanostructures as Prototypical Chiral Near-Field Sources, ACS Photonics, vol. 1, No. 6, pp. 530-537; 2014.

Schaferling, M. et al., Tailoring Enhanced Optical Chirality: Design Principles for Chiral Plasmonic Nanostructures, Physical Review X, vol. 2, No. 3, 031010; 2012.

Shen, J.T. et al., Mechanism for designing metallic metamaterials with a high index of refraction, Physical Review Letter, vol. 94, 197401; 2015.

Stephens, P.J. et al., The determination of the absolute configurations of chiral molecules using vibrational circular dichroism (VCD) spectroscopy, Chirality, vol. 20, No. 5, pp. 643-663; 2008.

Tang, Y. et al., Chiroptical hot spots in twisted nanowire plasmonic oscillators, Applied Physics Letters, vol. 102, No. 4, 043103; 2013.

Tang, Y. et al., Enhanced Enantioselectivity in Excitation of Chiral Molecules by Superchiral Light, Science, vol. 332, pp. 333-336; 2011.

Tang, Y. et al., Optical Chirality and Its Interaction with Matter, Physical Review Letters, vol. 104, 163901; 2010.

Tkachenko, G. et al., Optofluidic sorting of material chirality by chiral light, Nature Communications, vol. 5, 3577; 2014.

Wang, S.B. et al., Lateral optical force on chiral particles near a surface, Nature Communications, vol. 5, 3307; 2014.

Wei, X. et al., A high refractive index metamaterial at visible frequencies formed by stacked cut-wire plasmonic structures, Applied Physics Letters, vol. 97, No. 1, 011904; 2010.

Weiting, F. et al., Temperature effects on the refractive index of lead telluride and zinc selenide, Infrared Physics, vol. 30, No. 4, pp. 371-373; 1990.

(56) References Cited

OTHER PUBLICATIONS

Wen, F. et al., Plasmon transmutation: inducing new modes in nanoclusters by adding dielectric nanoparticles, Nano Letters, vol. 12, No. 9, pp. 5020-5026; 2012.

Zhao, Y. et al., Enantioselective Optical Trapping of Chiral Nanoparticles with Plasmonic Tweezers, ACS Photonics, vol. 3, No. 3, pp. 304-309; 2016.

Zhdanov, D.V. et al., Absolute asymmetric synthesis from an isotropic racemic mixture of chiral molecules with the help of their laser orientation-dependent selection, The Journal of Chemical Physics, vol. 127, No. 24, 244312 doi: 10.1063/1.2801640.; 2007.

Zhou, J. et al., Saturation of the magnetic response of split-ring resonators at optical frequencies, Physical Review Letters, vol. 95, 223902; 2005.

* cited by examiner

ENANTIOSELECTIVE DESTRUCTION OF CHIRAL MOLECULES

PRIORITY AND CROSS REFRENCE TO RELATED APPLICATIONS

This application claims the benefit of U.S. Provisional Application 62/302,108, which was filed on Mar. 1, 2016, and which is hereby incorporated by reference in its entirety.

STATEMENT REGARDING FEDERALLY SPONSORED R&D

This invention was made with Government support under contract 1151231 awarded by the national Science Foundation. The Government has certain rights in the invention.

BACKGROUND

Field

The disclosure generally relates to methods and devices for enrichment of one enantiomer of a chiral compound by selective photo-destruction of the other enantiomer of the compound.

Description of the Related Art

In biological systems, structure often dictates function. One fundamental component of a molecule's structure is its chirality. Chiral molecules occur as enantiomers, or molecular pairs of non-superimposable mirror images, perform different biological functions due to the chiral specificity of molecular receptors. This is particularly important in the pharmaceutical industry, where the efficacy of drugs is often affected by the presence of the opposite enantiomer, which may introduce unwanted or even harmful side effects.

SUMMARY

In some embodiments, a method for selective photo-destruction of one chiral enantiomer of a compound is provided. In some embodiments, the method comprises providing a solution comprising two chiral enantiomers of the compound, adding a nanostructure to the solution, irradiating the solution with a circularly polarized light, and exposing the solution to a local electric field and a local magnetic field, such that the circularly polarized light is differentially absorbed by the one chiral enantiomer, thereby achieving the selective photo-destruction of the one chiral enantiomer of the compound.

In some embodiments of the method, the nanostructure supports optical frequency electric resonances and optical frequency magnetic resonances. In some embodiments of the method, the nanostructure is excited with the circularly polarized light, thereby causing interference between the optical frequency electric resonances and optical frequency magnetic resonances. In some embodiments of the method, an amount of differential absorption of the circularly polarized light by the one chiral enantiomer and a rate of differential absorption of the circularly polarized light by the one chiral enantiomer are enhanced. In some embodiments of the method, the amount of differential absorption of the circularly polarized light by the one chiral enantiomer is enhanced about 17-fold to about 510-fold. In some embodiments of the method, the rate of differential absorption of the circularly polarized light by the one chiral enantiomer is enhanced about 2-fold to about 21-fold.

In some embodiments of the method, the nanostructure is provided as an array or as a suspension. In some embodiments of the method, the selective photo-destruction is one of photolysis, photoionization, or another selective photochemical process. In some embodiments of the method, the circularly polarized light in the UV range or in the IR range of the electromagnetic spectrum. In some embodiments of the method, photolysis is achieved by the circularly polarized light in the IR range. In some embodiments of the method, photoionization is achieved by the circularly polarized light in the UV range. In some embodiments of the method, the nanostructure is a nanosphere, nanocylinder, nanoplate, nanoshell, nanorod, nanorice, nanofiber, nanowire, nanopyramid, nanoprism, nanostar, nanocrescent, nanoring, nanoantenna, or a combination thereof. a size of the nanostructure ranges from about 1 nm to about 10,000 nm.

In some embodiments, a method for selective enrichment of one chiral enantiomer of a compound is provided. In some embodiments, the comprises providing a racemic solution comprising first and second chiral enantiomers of the compound, adding a nanostructure to the solution, irradiating the solution with a circularly polarized light, and exposing the solution to a local electric field and a local magnetic field, such that the circularly polarized light is differentially absorbed by the first chiral enantiomer, resulting in the selective photo-destruction of the first chiral enantiomer of the compound, thereby achieving enrichment of the second chiral enantiomer a compound.

In some embodiments, a device for selective photo-destruction of one chiral enantiomer of a compound is provided. In some embodiments, the device comprises an array of nanostructures, a suspension of nanostructures or a combination thereof, and a source of circularly polarized light. In some embodiments of the device, the nanostructures support optical frequency electric resonances and optical frequency magnetic resonances. In some embodiments of the device, the nanostructures can be excited with the circularly polarized light, thereby causing interference between the optical frequency electric resonances and optical frequency magnetic resonances.

In some embodiments of the device, an amount and a rate of differential absorption of the circularly polarized light by the one chiral enantiomer are enhanced. In some embodiments of the device, the nanostructures are nanospheres, nanocylinders, nanoplates, nanoshells, nanorods, nanorices, nanofibers, nanowires, nanopyramids, nanoprisms, nanostars, nanocrescents, nanorings, nanoantennas, or a combinations thereof. In some embodiments of the device, a size of the nanostructure ranges from about 1 nm to about 10,000 nm. In some embodiments of the device,a number of nanostructures in the array ranges from about 1 to about 1×10e14. In some embodiments of the device, a concentration of nanostructures in the suspension ranges from about 1 µL to about 1×10e15/µL. In some embodiments of the device, the selective photo-destruction of the one chiral enantiomer of the compound, and can result in the selective enrichment of the other chiral enantiomer of the compound.

BRIEF DESCRIPTION OF THE DRAWINGS

FIG. 3(b) shows spectrum of spatial maxima of CD enhancements.

FIG. 3(c) shows spectrum of spatial maxima of dissymmetry factor enhancements, with the requirement that the electric field magnitude be greater than that of the incident field at that point. Wavelength locations of the peak enhancements in CD and the dissymmetry factor occur near peaks of magnetic Mie resonances, as indicated by dashed lines.

FIG. 4(a)-FIG. 4(c) show electric field enhancement $|\tilde{E}|/|\tilde{E}_{inc}|$ at wavelengths corresponding to peak CD enhancements.

FIG. 4(d)-FIG. 4(f) show CD enhancement at wavelengths of λ=1684.5, 1390.0, and 1192.8 nm, from top to bottom.

FIG. 4(g)-FIG. 4(i) show electric field enhancement at wavelengths corresponding to peak dissymmetry factor enhancements.

FIG. 4(j)-FIG. 4(l) show dissymmetry factor enhancement at wavelengths of λ=1690.7, 1391.8, and 1193.4 nm, from top to bottom.

FIG. 5 (top) shows spectrum of spatial maxima in dissymmetry factor, $g=g_{CPL}$, with the requirement that the electric field magnitude be greater or equal to that of the incident field for a particle with no electric-type resonances. FIG. 5 (bottom) shows spectrum of spatial maxima in dissymmetry factor enhancement, $g=g_{CPL}$, with the requirement that the electric field magnitude be greater or equal to that of the incident field for a particle with no magnetic-type resonances.

DETAILED DESCRIPTION

Figure 1:
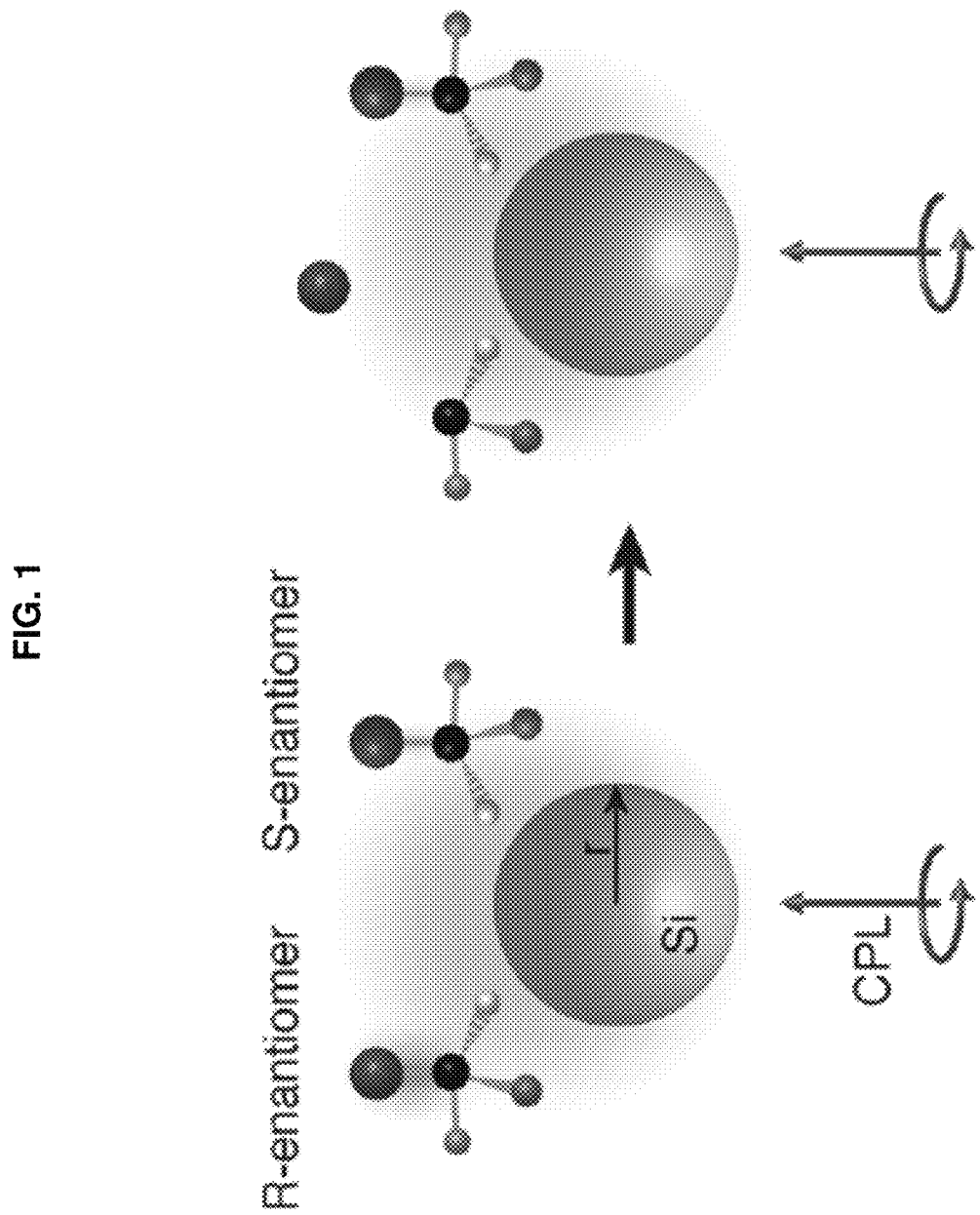
FIG. 1 shows a schematic for photolysis of a molecule near a silicon nanosphere of radius r illuminated by circularly polarized light.

In biological systems, structure often dictates function. One fundamental component of a molecule's structure is its chirality. Molecules with a specific "handedness" or chirality, play a critical role in chemical and biological processes. Enantiomers are molecular pairs of non-superimposable mirror images with opposite chirality, which perform different biological functions due to the chiral specificity of molecular receptors. This is particularly important in the pharmaceutical, chemical, and agricultural industries, where the efficacy of drugs is often affected by the presence of the opposite enantiomer, which may introduce unwanted or even harmful side effects.[1,2]

Separation of enantiomers is non-trivial as they are identical in all scalar physical properties such as molecular mass, boiling or freezing points, and charge. However, separation of chiral molecules is of high importance due to the differing biological functions of the opposite enantiomers of a compound. Separating enantiomers is crucial and of paramount importance to the pharmaceutical, chemical and agricultural industries, but prevailing chemical methods are economically costly and time-consuming. Confirmation of enantiopure products is of equal importance and accomplished via circular dichroism (CD) spectroscopy. However, the sensitivity of CD spectroscopy is limited and requires high sample concentrations.

While nature routinely produces only one enantiomer for a given function (i.e., all amino acids are "left-handed" while sugars are "right-handed"), standard laboratory syntheses generally produce a racemic (i.e., 50-50) mixture of enantiomers. Thus, separation techniques for a molecule rely on the molecule's unique enantiomeric interaction with another chiral element, typically another molecule. Thus, techniques for the separation of the enantiomers of a compound rely on enantiomeric interactions (e.g., the interaction of the enantiomers of the compound) with another chiral element. Other chiral elements are typically other molecules in an enantiopure solution form. Compatible chiral substrates must be developed for each target molecule, a trial-and-error process that is generally time-consuming and expensive.[4] Commonly used chemical separation techniques such as high performance liquid chromatography (HPLC) rely on the availability of compatible chiral substrates for each target molecule. The resulting trial and error process of finding a suitable substrate can be time consuming and expensive due to the high cost of chiral columns.[3,4] For example, chiral columns in chromatography are about five times the cost of their achiral counterparts.[52]

A promising alternative to chemical based separation methods is to exploit the chiral properties of light and chiral light-matter interactions. In particular, chiral molecules can be considered as electric ($p_e$) and magnetic ($p_m$) dipoles: one enantiomer has $p_e$ and $p_m$ aligned in-phase while the other has $p_e$ and $p_m$ out-of-phase. This difference in dipole alignment leads to a difference in absorption of circularly polarized light (CPL), a phenomenon described by Kuhn's dissymmetry factor.[6] When a racemic mixture is illuminated by CPL of one handedness, one enantiomer will absorb more optical energy than the other, enabling selective photolysis or photoionization of that enantiomer. Thus, opposite enantiomers exhibit preferential absorption of either left or right circularly polarized light (L-/R-CPL), a phenomenon described by Kuhn's dissymmetry factor and measured using CD spectroscopy.[5-7]

Illumination with CPL provides a potentially cost-effective and versatile alternative platform for differentiating between enantiomers. However, the interaction of light with the molecule's magnetic dipole is approximately 10,000 times weaker than its interaction with the electric dipole, implying that the molecules appear as near-identical electric dipoles to the optical illumination. CPL alone can only achieve enantiomeric excesses up to 2% with substantial yield.[6] Higher excesses can be reached, but at the cost of final product yield.[6] For example, higher excesses can be reached, but require photolysis of 99% of the reactants, leaving only a 1% yield, too low for commercial use.[8,9]

Recently, it has been experimentally shown that Kuhn's dissymmetry factor can be enhanced 11 times beyond that of CPL by employing a standing wave of elliptically polarized light.[10] However, this technique relies on minimizing electric field strength rather than enhancing the preferential absorption between enantiomers. The resulting low molecular absorption in regions with enhanced dissymmetry factor limit the efficiency of any photoseparation process.[11]

Alternatively, plasmonic structures have been extensively studied for enhancing chiral spectroscopic measurements,[12-19] as well as enhancing optical enantioselective forces[20-22] exerted by polarized light.[23-26] Some chiral plasmonic structures have been shown to enhance the dissymmetry factor up to 7-fold,[27] but the reported enhancements are spatially correlated with field strengths below incident field strengths. Therefore, a molecule near these plasmonic structures would absorb less light than when illuminated with CPL alone, resulting in a lengthy separation process. Additionally, if the external illumination power were to be increased in order to achieve higher absorption efficiencies in both the standing wave and plasmonic systems, nearby field hot spots would destroy both enantiomers, leading to low yields.

The chirality of light can be enhanced beyond that of CPL, resulting in a corresponding increase in the absorption difference between opposite enantiomers in a racemic mixture that is illuminated. By enhancing the rate of differential absorption, the achievable enantiomeric excess can also be enhanced beyond that achieved with using CPL alone. Described herein is a circularly polarized light-driven separation of enantiomers using magnetically excited modes in dielectric particles that have achiral geometries.

In some embodiments, an optical platform to efficiently separate chiral molecules is disclosed. In some embodiments, the optical platform is a light-mediated separation technique based on using engineered nanostructures (e.g., nanomaterials, metamaterials, etc.), also reference to herein as nanoparticles or high index dielectric nanoparticles, to enhance the chirality of incident light (e.g., CPL). In order to achieve enhancements beyond inherent levels of enhancement with CPL alone, the nanoparticles support both magnetic resonances as well as electric resonances.

As referred to herein, nanostructures are not just nanoparticles, but any nanostructure that supports optical frequency magnetic resonances are contemplated. In some embodiments, any nanostructure that supports both optical frequency electric resonances and optical frequency magnetic resonances are also contemplated.

FIG. 1 shows a schematic for photolysis of a molecule near a silicon nanosphere of radius r illuminated by circularly polarized light. The silicon nanosphere is illuminated with CPL of a certain wavelength. In some embodiments, Mie theory is used to calculate the rate of differential absorption 'g' (also known as Kuhn's dissymmetry factor) near silicon nanospheres. The rate of differential absorption is optimized over space, wavelength of the CPL, and particle size, while imposing the limitation that the electric field has a magnitude that is at least equal to or greater than the magnitude of the incident excitation.

The resultant effect is that when a racemic mixture is illuminated by one handedness (either right or left) of CPL, one enantiomer will absorb more energy than the other enantiomer. In some embodiments, the separation technique uses dielectric nanoparticles that support optical frequency magnetic and electric Mie resonances to provide enhanced light chirality. In some embodiments, the light driven chiral resolution uses optical frequency magnetic and electric Mie resonances in dielectric nanoparticles that have achiral geometries. The enhanced light chirality is provided while maintaining electric and magnetic field strengths equal to or greater than that of the illuminating field. In some embodiments, the illuminating field can be from any light source including, without limitations, a natural light source, or a lamp (e.g., without limitations, an LED, a lamp, or a laser). In some embodiments, the available range of strengths of the electric and magnetic fields provided by these sources of illumination are sufficient to practice the various aspects of the invention provided herein.

The difference in absorption of CPL has the potential to photoionize or photolyse one of the enantiomers, leading to an excess of the other enantiomer in the solution. In some embodiments, by selecting the appropriate particle size and excitation wavelength, it is possible to either photoionize or photolyze one enantiomer while leaving the other intact. In some embodiments, the separation technique is based on increasing the Kuhn's dissymmetry factor (g; See, Examples). In some embodiments of the separation technique, increasing the dissymmetry factor results in selectively photoionizing one enantiomer in a racemic mixture while leaving the other intact (FIG. 1). In some embodiments of the separation technique, increasing the dissymmetry factor results in selectively photolyzing one enantiomer in a racemic mixture while leaving the other intact (FIG. 1).

Figure 2:
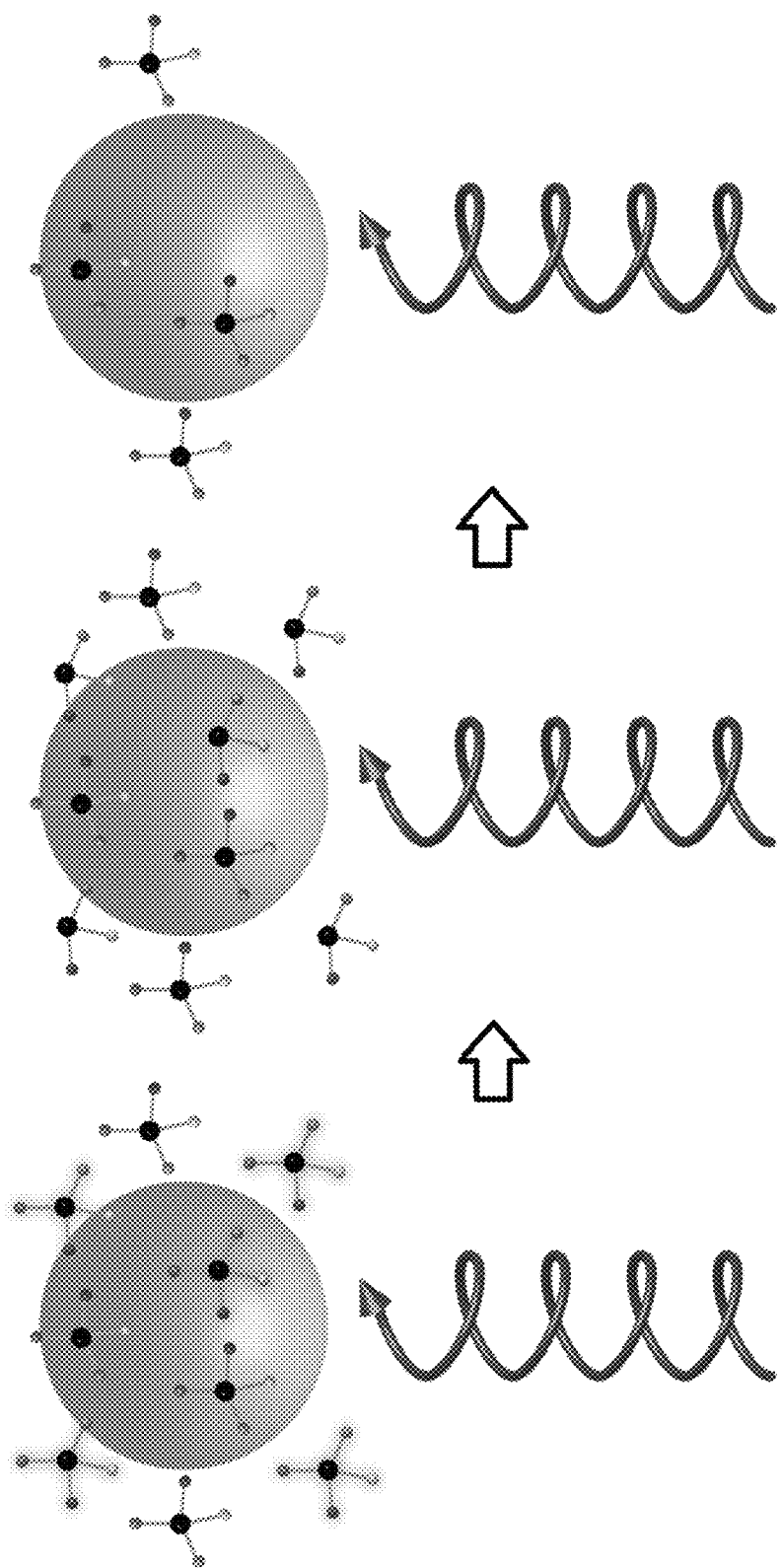
FIG. 2 shows preferential absorption and separation of enantiomers by photolysis of a chiral enantiomer in a racemic solution.

FIG. 2 shows a schematic of an embodiment of a separation process by photolysis. Incident CPL is absorbed by the target enantiomer to be photolysed, leading to dissociation of a bond in that molecule. In some embodiments, one enantiomer selectively absorbs incident photons (FIG. 2; left) causing the breakage of a bond in that enantiomer (FIG. 2; middle) allowing separation of the enantiomers based on one or more differences in their properties (FIG. 2; right).

In some embodiments, the solution can be a mixture of two enantiomers in liquid form, a mixture of two enantiomers in gas form, or some other mixture of two enantiomers. The induced physical difference in charge or molecular weight can then be used to separate the previously racemic mixture into enantiopure solutions. Thus, the enantiomers in resulting solution can then be separated based on physical properties. These physical properties include, but are not limited to, charge, molecular weight, mass, etc. For example, in some embodiments, enantiomers in the resulting solution can then be separated by charge. In some embodiments, enantiomers in the resulting solution can then be separated by molecular weight. In some embodiments, enantiomers in the resulting solution can then be separated by mass. In some embodiments, enantiomers in resulting solution can then be separated by charge, molecular weight and mass. In some embodiments, this separation is achieved by one or more methods known in the art, including without limitations, distillation chromatography, gas chromatography, liquid chromatography or a combination thereof.

In some embodiments, to increase Kuhn's dissymmetry factor, nanostructures that support strong optical-frequency magnetic resonances as used. In some embodiments, the nanostructures are suspended in solution. In some embodiments, the nanostructures are patterned as an array. In some embodiments, the array is provided on a substrate. In some embodiments, the array is provided in solution. In some embodiments, the array is in close proximity to the racemic mixture.

In some embodiments, a device for the separation of the enantiomers of a compound is provided. In some embodiments, the device comprises an array of nanostructures. In some embodiments, the device has an array on a substrate. In some embodiments, the device has a solution comprising the array.

In some embodiments, the separation scheme is a suspension in which nanostructures can be used to generate large spatial regions of improved performance compared to CPL. In some embodiments, the separation scheme is a planar array in which nanostructures can be used to generate large spatial regions of improved performance compared to CPL. In some embodiments, the separation scheme is a combination of suspension and planar array in which nanostructures can be used to generate large spatial regions of improved performance compared to CPL. In some embodiments, the large spatial regions of improved performance reach up to about 320 nm from the surface of the nanostructures. In some embodiments, the large spatial regions of improved performance reach about 10, 20, 40, 80, 160 or 320 nm from the surface of the nanostructures. In some embodiments, smaller or larger spatial regions of improved performance are contemplated from the surface of the nanostructures. For example, the spatial regions of improved performance reach from about 1 nm to about 1000 nm from the surface of the nanostructures. In some embodiments, the spatial regions of improved performance reach from about 500 nm to about 5000 nm from the surface of the nanostructures. In some embodiments, the spatial regions of improved performance reach from about 0.5 nm to about 5000 nm from the surface of the nanostructures. In some embodiments, the spatial regions of improved performance reach from about 0.5, 1, 5, 10, 25, 50, 75 100, 150, 200, 250, 300, 350, 400, 500, 600, 700, 800, 900, 1000, 1500, 2000, 2500, 3000, 3500, 4000, 4500 or 5000 nm from the surface of the nanostructures, or within a range defined by any two of the aforementioned values.

In some embodiments, a high-throughput system comprising a device comprising an array of nanoparticles or a suspension of nanoparticles (e.g., nanospheres) can be generated to enable high-throughput, cost effective separation of chiral molecules based on the teachings of the present disclosure. In some embodiments, an optimization of the array spacing would depend on the overlap of regions of high enhancement from neighboring nanostructures and the volume throughput of the system. In some embodiments, an optimization of the array dimensions and/or shape would depend on the overlap of regions of high enhancement from neighboring nanostructures and the volume throughput of the system. In some embodiments, an optimization of the concentration of nanoparticles in the suspension would depend on the overlap of regions of high enhancement from neighboring nanostructures and the volume throughput of the system. In some embodiments, an optimization of the dimensions of the nanoparticles in the array or the suspension would depend on the overlap of regions of high enhancement from neighboring nanostructures and the volume throughput of the system. Since the maximum value of $g/g_{CPL}$ (See, Examples) occurs at the surface of the nanoparticle, a closely-packed array or a more concentrated suspension would yield the highest reaction selectivity but would limit the available reactant volume. Thus, in some embodiments, the system comprises a closely-packed array of nanostructures. In some embodiments, the system comprises a concentrated suspension of nanostructures. In some embodiments, the system comprises a closely-packed array of nanostructures optimized to enable high-throughput, cost effective separation of chiral molecules. In some embodiments, the system comprises a concentrated suspension of nanostructures optimized to enable high-throughput, cost effective separation of chiral molecules.

In some embodiments, each nanostructure in the array has a dimension of about 10 nm to about 10 µm. In some embodiments, each nanostructure in the array has a dimension of about 10, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500 or 10000 nm, or within a range defined by any two of the aforementioned values.

In some embodiments, the array has a size of about 10 nm to about 10 cm. In some embodiments, the array has size of about 10 nm, 100 nm, 500 nm, 1 µm, 5 µm, 10 µm, 50 µm, 100 µm, 500 µm, 1 mm, 10 mm, 5 mm, 10 mm, 50 mm, 100 mm, 500 mm, 1 cm, 5 cm or 10 cm, or within a range defined by any two of the aforementioned values. In some embodiments, the array can have any shape that can be achieved in the art. Non-limiting examples include cube, cuboid, tetrahedron, pyramid, square pyramid, hexagonal pyramid, prism, triangular prism, pentagonal prism, hexagonal prism, octahedron, dodecahedron, sphere, ellipsoid, cone, cylinder and icosahedron.

In some embodiments, the number of nanostructures in an array can range from about 1 to about 1×10e14. In some embodiments, the number of nanostructures in an array can range from about 1, 100, 500, 1×10e3, 5×10e3, 1×10e4, 5×10e4, 1×10e5, 5×10e5, 1×10e6, 5×10e6, 1×10e7, 5×10e7, 1×10e8, 5×10e8, 1×10e9, 5×10e9, 1×10e10, 5×10e10, 1×10e11, 5×10e11, 1×10e12, 5×10e12, 1×10e13, 5×10e13 or 1×10e14, or within a range defined by any two of the aforementioned values. In some embodiments, the concentration of nanostructures in the reaction solution can range from about 1/µL to about 1×10e15/µL.

In some embodiments, the concentration of nanostructures in the reaction solution can range from about 1, 100, 500, 1×10e3, 5×10e3, 1×10e4, 5×10e4, 1×10e5, 5×10e5, 1×10e6, 5×10e6, 1×10e7, 5×10e7, 1×10e8, 5×10e8, 1×10e9, 5×10e9, 1×10e10, 5×10e10, 1×10e11, 5×10e11, 1×10e12, 5×10e12, 1×10e13, 5×10e13 or 1×10e14 5×10e14 or 1×10e15/µL, or within a range defined by any two of the aforementioned values.

In some embodiments, the array of nanoparticles can be based on other types of nanostructures including, but not limited to nanospheres, nanocylinders, nanoplates, nanoshells, nanorods, nanorice, nanofibers, nanowires, nanopyramids, nanoprisms, nanostars, nanocrescents, nanorings, nanoantennas, or a combination thereof. In some embodiments, the present disclosure can be extrapolated to nanoparticle arrays based on other types of nanostructures, particle arrays and metasurfaces to achieve a large-area enhancement of g.

In the reaction, the nanostructures in solution or an array are not functionalized, attached, or conjugated to the enantiomers. Thus, the nanostructures can be readily removed from the reaction upon completion of the reaction. In some embodiments, the nanostructures are not functionalized, attached, or conjugated to the enantiomers and can be readily removed from the reaction solution and reused. In some embodiments, any size-based separation method known in the art can be used. Non-limiting examples include filtration, chromatography and centrifugation.

In some embodiments, one nanostructure is appropriate for one phase of the reaction and another nanostructure is appropriate for another phase of the reaction. In some embodiments, the nanostructure is destroyed and/or lost over the course of the reaction, and therefore, the concentration, dimensions, effectiveness, or other properties of the nanostructure that are required for the reaction are compromised and/or lost and/or adversely affected. Thus, in some embodiments, the nanostructure present during the initial part of the reaction is removed and replaced with the same or different nanostructure. In some embodiments, combinations of different nanostructures are used.

In some embodiments, the reaction comprises a pharmaceutical composition. In some embodiments, the nanostructures can be readily removed from the pharmaceutical composition before administration of the pharmaceutical composition. In some embodiments, the nanostructures can be readily removed from the pharmaceutical composition before administration of the pharmaceutical composition. In some embodiments, the nanostructures increase the efficacy, potency, bioavailability, pharmacokinetics, pharmacodynamics, and/or one/or more other desirable properties, and reduce toxicity, side effects, and/or one/or more other undesirable properties of one or more drugs in a pharmaceutical composition. In some embodiments, the nanostructures can reduce the toxicity and environmental impact of herbicides. In some embodiments, the nanostructures can reduce the toxicity and environmental impact of pesticides.

In some embodiments, a system based on the use of dielectric nanoparticles provided herein can enable high-throughput, cost effective separation of chiral molecules, furthering advancements in natural product synthesis and pharmaceutics. The constituents of the nanomaterials have proven to be non-toxic till date. Silicon is a commonly used material, and has been shown to be non-toxic. Therefore, in some embodiments, the nanoparticles are silicon nanoparticles. In some embodiments, the nanoparticles are non-toxic silicon nanoparticles.

In some embodiments, identified herein are the necessary conditions for enhancing Kuhn's dissymmetry factor using computation approaches to understand molecule-nanostructure interactions. Optical-frequency magnetic resonances are key in achieving simultaneously high dissymmetry factors and efficient molecular absorption.[55]

In some embodiments, identification of necessary conditions for enhancement of g in a model system of silicon nanospheres is provided. Importantly, g can be enhanced while maintaining field strength similar to that of the incident field, allowing for efficient total absorption. In some embodiments, peak enhancements in g occur near but not exactly on magnetic resonances such that the C is enhanced while electric field strengths are near incident field strengths. Additionally, high-index materials with low losses are ideal for achieving high enhancements of g. In some embodiments, a key design criterion for enhancing the dissymmetry factor is to be near but not exactly on the particle's resonance, where C remains large, but $|\tilde{E}|/|\tilde{E}_{inc}|$ is near unity (See, Example 4). In some embodiments, larger values of $g/g_{CPL}$ can be expected at small spectral shifts from each magnetic resonance, where the electric field enhancements are closer to unity (See, Example 6). In some embodiments, larger field enhancements occur at peak wavelengths for $C/C_{CPL}$. In some embodiments, smaller field enhancements at peak wavelengths for $g/g_{CPL}$ occur closer to peak magnetic resonance wavelengths, leading to larger field enhancements.

In some embodiments, high-refractive-index nanospheres illuminated with CPL can locally enhance Kuhn's dissymmetry factor while maintaining the total energy absorbed. In some embodiments, these spatially varying enhancements can be correlated with excitation of magnetic Mie resonances within the nanospheres. In some embodiments, these spatially varying enhancements are not global. In some embodiments, these spatially varying enhancements are local. In some embodiments, the size of the nanosphere can be varied.

In some embodiments, by increasing the differential absorption between enantiomers, the device can either eject an electron or repeatedly excite a vibrational mode to break a bond. This results in photoionization or photolysis of one enantiomer while the other enantiomer is remains intact.

By selecting the appropriate particle size and excitation wavelength, it is possible to either photoionize or photolyse one enantiomer while leaving the other intact. In some embodiments, the size of the nanoparticle can range from about 10 nm to about 10,000 nm. In some embodiments, the nanoparticles can have a size in a range of about 10 nm to 3000 nm, 10 nm to 1000 nm, 50 nm to 1500 nm, 100 nm to 2000 nm, 100 nm to 2500 nm, 100 nm to 3000 nm, 100 nm to 5000 nm, 150 nm to 2500 nm, 100 to 7000 nm, 100 nm to 9000 nm or 100 nm to 10,000 nm, or within a range defined by any two of the aforementioned values. In some embodiments, the nanoparticles can have a size of about, 1, 5, 10, 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10000 nm, or within a range defined by any two of the aforementioned values.

Figure 6:
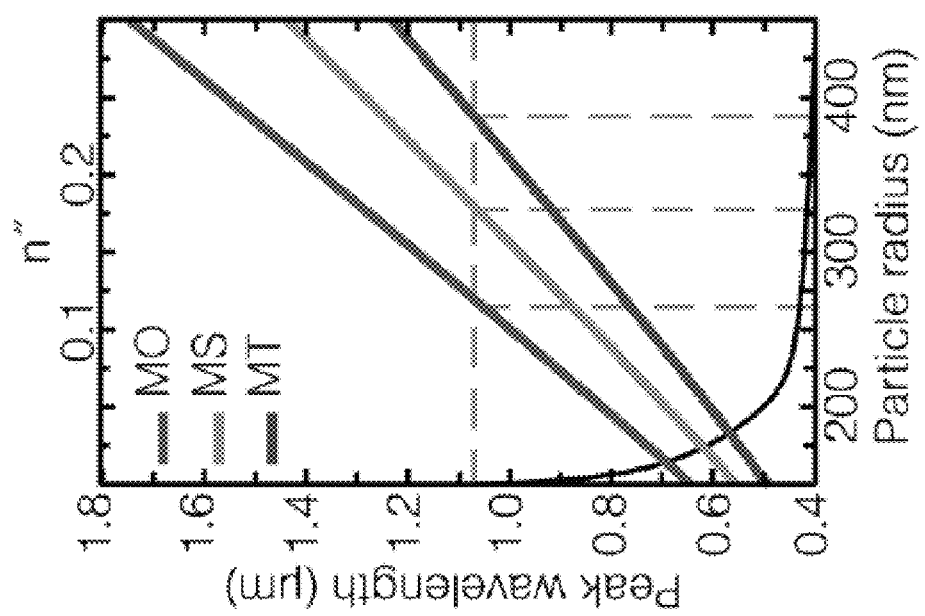
FIG. 6 shows wavelength positions of dissymmetry factor enhancement peaks can be shifted by changing particle radius, allowing specific tuning to different molecular resonances.
Figure 7:
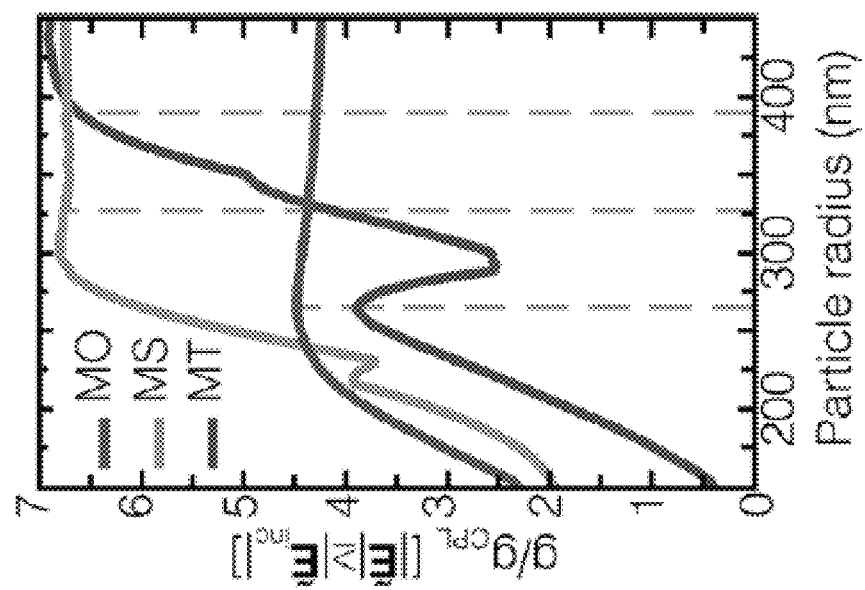
FIG. 7 shows peak dissymmetry factor enhancements increase with increasing silicon particle size, then saturate. Maximum enhancement achieved for the MS-and MT-associated peaks is roughly 7-fold.

FIG. 6 shows wavelength positions of differential absorption enhancement can be shifted by changing particle radius this allows specific tuning to different molecular resonances. FIG. 7 shows peak differential absorption enhancement values. In some embodiments, the absorption increase with increasing silicon particle size, then stabilize. In some embodiments, the maximum enhancement is about 7-fold. In some embodiments, lower enhancement values are likely due to losses in the material. Thus, In some embodiments, a low loss, high index dielectric material could provide greater enhancements.

By varying the critical dimensions of the nanostructure, the optical resonances can be tuned from ultraviolet to infrared frequencies, matching either molecular vibrational resonances for photolysis or molecular electronic resonances for photoionization. Importantly, both vibrational and electronic resonances can be easily measured for chiral molecules, eliminating the trial-and-error process of standard chromatography approaches.

In some embodiments, an enhancement of the differential absorption of opposite enantiomers is provided for the purpose of selectively photoionizing or photolysing one enantiomer in a racemic solution. In some embodiments, by varying the nanosphere size, the Mie resonances can be tuned from IR to UV wavelengths to match either molecular vibrational resonances for photolysis or molecular electronic resonances for photoionization. In some embodiments, the IR wavelength range is from about 750 nm to about 100 μm of the electromagnetic spectrum. In some embodiments, the UV wavelength is from about 10 nm to about 400 nm of the electromagnetic spectrum. In some embodiments, the visible wavelength range is from about 400 nm to about 750 nm of the electromagnetic spectrum.

In some embodiments, IR wavelengths result in photolysis. In some embodiments, UV wavelengths result in photoionization. In some embodiments, the nanosphere size is such that the Mie resonances match molecular vibrational resonances for photolysis. In some embodiments, the nanosphere size is such that the Mie resonances match molecular electronic resonances for photoionization. In some embodiments, the wavelengths are in the visible range. In some embodiments, the wavelengths are in the IR range. In some embodiments, the wavelengths are in the UV range. In some embodiments, the wavelengths are a combination of visible, IR and/or UV wavelength ranges. In some embodiments, the design parameters described herein (e.g., Example 3) can be extrapolated to the UV spectral regime to selectively photoionize enantiomers. In some embodiments, the design parameters described herein (e.g., Example 3) can be extrapolated to the visible spectral regime to selectively photoionize enantiomers.

Inherent differential absorption of CPL alone by enantiomers is generally very low can only achieve enantiomeric excesses only up to about 2%. In some embodiments, there is no enhancement (or equivalently, a 1-fold enhancement) without dielectric nanoparticles. Therefore, any enhancement given by the nanoparticles is calculated as an enhancement compared to the case without dielectric nanoparticles. The ability to maintain local field strengths above the incident field while simultaneously enhancing the dissymmetry factor appears to be unique to nanostructures with both magnetic and electric resonances. Thus, in some embodiments, nanostructures provide ability to maintain local field strengths above the incident field while simultaneously enhancing the dissymmetry factor with both magnetic and electric resonances. In some embodiments, the enantiomeric excess can range from about 5% to about 25%. In some embodiments, the enantiomeric excess can range from about 25% to about 50%. In some embodiments, the enantiomeric excess can range from about 50% to about 75%. In some embodiments, the enantiomeric excess can range from about 75% to about 100%. In some embodiments, the enantiomeric excess can be about 5, 10, 15, 20, 25, 30, 35, 40, 45, 50, 55, 60, 65, 70, 75, 80, 85, 90, 95 or 100%, or within a range defined by any two of the aforementioned values. In some embodiments, the yield of the desired enantiomer can range from about 5% to about 100%. In some embodiments, the yield of the desired enantiomer can be about 5, 10, 15, 20, 25, 30, 35, 40, 45, 50, 55, 60, 65, 70, 75, 80, 85, 90, 91, 92, 93, 94, 95, 96, 97, 98, 99 or 100%, or within a range defined by any two of the aforementioned values.

The optimization of differential absorption reveals tunable spectral peaks in the local preferential absorption in chiral molecules. For example, for nanospheres with radii ranging from about 150 nm to about 450 nm, the tunable spectral peaks range from enhancements of about 4-fold to about 7-fold improvement as compared to CPL, and correspond in wavelength to the 8th, 16th, and 32nd order magnetically excited Mie resonances.

In some embodiments, alternate particle geometries could further improve this enhancement. In some embodiments, alternate particle geometries comprise nanodisks as possible alternate geometry. In some embodiments, alternate particle geometries can be anything that can support both magnetic resonances as well as electric resonances. Thus, in some embodiments, the geometry can comprise any one or more of the geometrical shapes disclosed herein (e.g., nanospheres, nanocylinders, nanoplates, nanoshells, nanorods, nanorice, nanofibers, nanowires, nanopyramids, nanoprisms, nanostars, nanocrescents, nanorings, nanoantennas, or a combination thereof).

In some embodiments, an enhancement of the differential absorption of opposite enantiomers for the purpose of selectively photoionizing or photolysing one enantiomer in a racemic solution is achieved using dielectric nanoparticles. In some embodiments, high-index dielectric nanoparticles increase enantiomeric excesses 7 times beyond CPL in free space. In some embodiments, Mie theory and a local optimization algorithm indicate that magnetic multipolar Mie resonances supported by submicrometer silicon spheres increase Kuhn's dissymmetry factor 7-fold, compared to CPL in free space. In some embodiments, an enhancement of the differential absorption of opposite enantiomers for the purpose of selectively photoionizing or photolysing one enantiomer in a racemic solution is about 2, 3, 4, 5, 6 or 7-fold including any value and range above and/or below any of the preceding values and any value and range between any two of the preceding values. In some embodiments, Kuhn's dissymmetry factor is increased about 2-fold to about 21-fold, compared to CPL in free space. In some embodiments, Kuhn's dissymmetry factor (also known as the rate of differential absorption) is increased about 1.25, 2.5, 5, 7.5, 10, 12.5, 15, 17.5, 20, 22.5, 25, 27.5, 30, 32.5, 35, 37.5, 40, 42.5, 45, 47.5 or 50-fold, compared to CPL in free space, or within a range defined by any two of the aforementioned values.

Further, in some embodiments, the circular dichroism signal (also known as the amount of differential absorption) can be enhanced about 170-fold. In some embodiments, the circular dichroism signal is enhanced about 17-fold to about 510-fold. In some embodiments, the circular dichroism signal is enhanced about 3.75, 7.5, 15, 30, 60, 90, 120, 150, 180, 210, 240, 270, 300, 330, 360, 390, 420, 450, 480, 510, 540, 570, 600, 630, 660, 690, 720, 750, 780, 810, 840, 870, 900, 930, 960 or 1020-fold, or within a range defined by any two of the aforementioned values. Importantly, in some embodiments, these local enhancements maintain the total molecular absorption rate, enabling efficient selective photoexcitation. Even greater enhancements in Kuhn's dissymmetry factor can be achieved with lower loss and higher refractive index nanoparticles. Thus, in some embodiments, a more efficient all-optical chiral resolution technique is provided.

Figure 3:
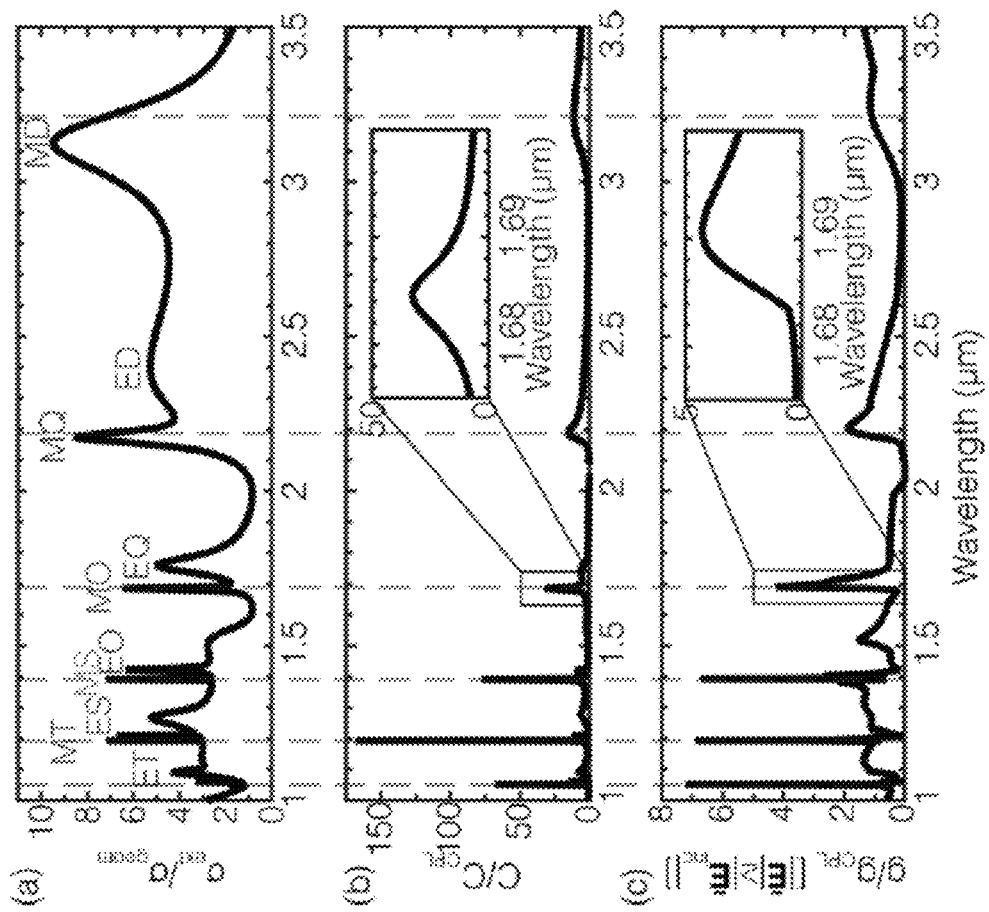
FIG. 3(*a*) shows total extinction cross-section of a silicon sphere. Contributing peaks are labeled as follows: magnetic dipole (MD), electric dipole (ED), magnetic quadrupole (MQ), electric quadrupole (EQ), magnetic octupole (MO), electric octupole (EO), magnetic 16-pole (MS), electric 16-pole (ES), magnetic 32-pole (MT), electric 32-pole (ET).

FIG. 3 (top) shows total extinction cross-section (top line) and individual magnetic and electric Mie resonance contributions to the extinction cross section of a silicon sphere. The individual magnetic and electric Mie resonance contributions are labeled as follows: magnetic dipole (MD), electric dipole (ED), magnetic quadrupole (MQ), electric quadrupole (EQ), magnetic octupole (MO), electric octupole (EO), magnetic 16-pole (MS), electric 16-pole (ES), magnetic 32-pole (MT), electric 32-pole (ET).

FIG. 3 (bottom) shows spatial maximum of differential absorption enhancement, with the requirement that the electric field magnitude be greater than that of the incident field at that point. In some embodiments, the wavelength locations of the peaks in differential absorption enhancement occur near peaks of higher order magnetic Mie resonances.

Figure 4:
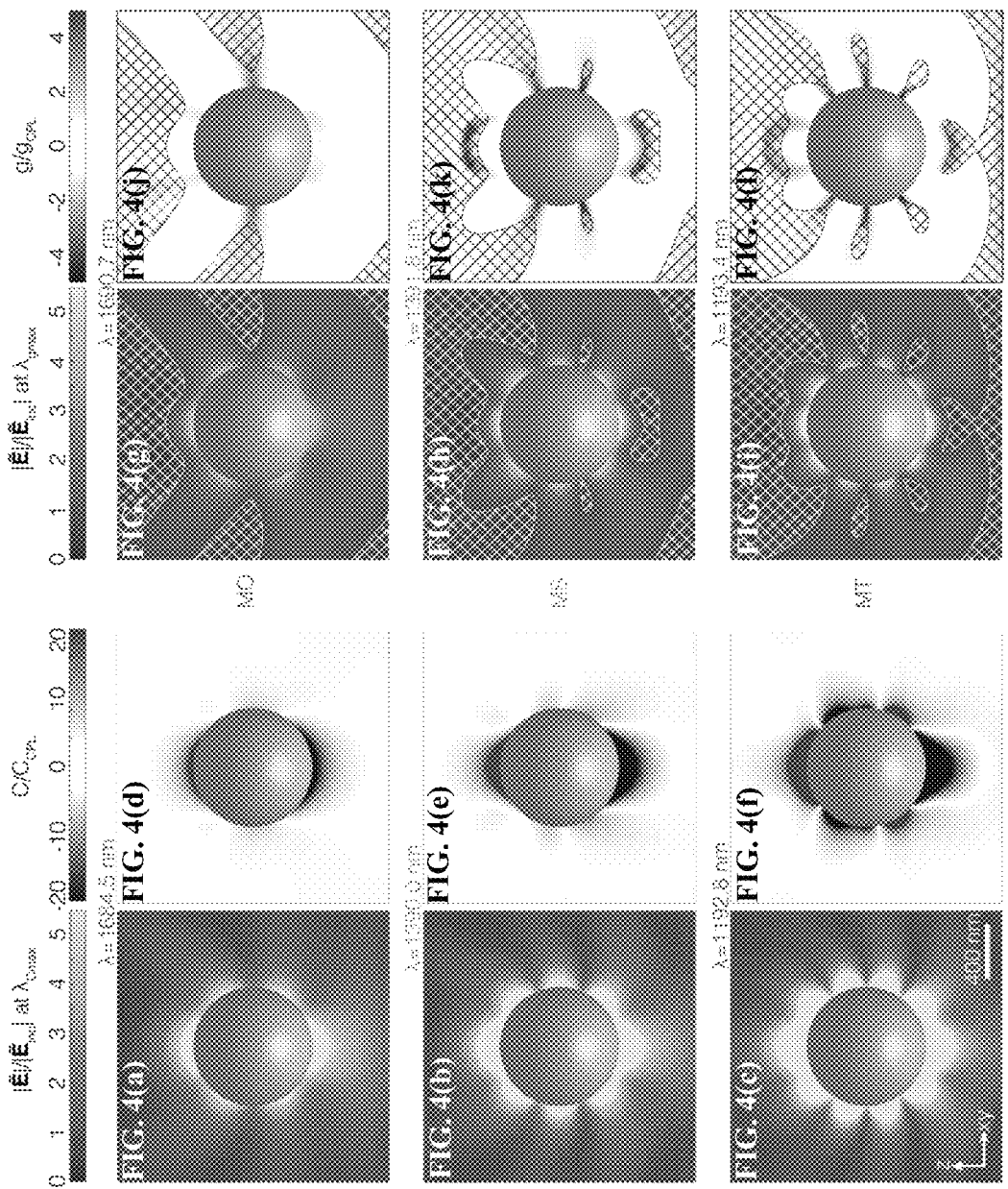
FIG. 4(a)-FIG. 4(l) show spatial distributions of electric field, CD, and dissymmetry factor enhancements for a silicon nanosphere illuminated from below with CPL.

FIG. 4 shows the spatial distributions of the electric field magnitude (left panel) and differential absorption between opposite enantiomers (right panel). Each plot from top to bottom in each panel corresponds to the peaks in differential absorption enhancement that correspond to the magnetic octupole (MO), magnetic 16-pole (MS), and magnetic 32-pole (MT) Mie resonances.

In some embodiments, enhancement of Kuhn's dissymmetry factor can be based on the order of magnetic mode. In some embodiments, enhancement of Kuhn's dissymmetry factor can be based on a lower order of magnetic mode (e.g., MO; FIG. 3 and FIG. 4). In some embodiments, lower order magnetic mode results in lower enhancement of g. In some embodiments, the lower enhancement of g is about 4-fold. In some embodiments, lower order magnetic mode has $g/g_{CPL}$ peaks that have broader line widths (e.g., MO-associated peak in $g/g_{CPL}$ lines has fwhm of 20 nm (FIG. 4). In some embodiments, lower order magnetic mode is more tolerable to differing excitation wavelengths. In some embodiments, lower order magnetic mode is more tolerable to differing excitation wavelengths sphere sizes. In some embodiments, lower order magnetic mode is more tolerable to differing excitation wavelengths and sphere sizes. In some embodiments, lower order magnetic mode provides less efficient preferential absorption.

In some embodiments, enhancement of Kuhn's dissymmetry factor can be based on a higher order of magnetic mode (e.g., MT and MS; FIG. 3 and FIG. 4). In some embodiments, higher order magnetic mode results in higher enhancement of g. In some embodiments, the higher enhancement of g is at least about 4-fold, at least about 5-fold, at least about 6-fold, at least about 7-fold, at least about 8-fold, at least about 9-fold or at least about 10-fold. In some embodiments, the enhancement of g is between about 4-fold and about 10-fold. In some embodiments, the enhancement of g is greater than about 10-fold. In some embodiments, the higher enhancement of g is at least about 4, 5, 6, 7, 8, 9, 10, 11, 12, 13, 14, 15, 16, 17, 18, 19 or 20-fold, or within a range defined by any two of the aforementioned values. In some embodiments, higher order magnetic mode has $g/g_{CPL}$ peaks that have narrower line widths (e.g., MS-associated peak in $g/g_{CPL}$ lines has fwhm of 3 nm and MT-associated peak in $g/g_{CPL}$ lines has fwhm of 2 nm; FIG. 4). In some embodiments, higher order magnetic mode is less tolerable to differing excitation wavelengths. In some embodiments, higher order magnetic mode is less tolerable to differing excitation wavelengths sphere sizes. In some embodiments, higher order magnetic mode is less tolerable to differing excitation wavelengths and sphere sizes. In some embodiments, higher order magnetic mode provides more efficient preferential absorption.

In some embodiments, a nanoparticle (e.g., a silicon sphere particle) can support only electric type resonances. In some embodiments, a particle can support only magnetic type resonances. In some embodiments, a particle can support both electric and magnetic type resonances. In some embodiments, high enhancements in g are observed for a silicon particle supporting both magnetic and electric type resonances. In some embodiments, high enhancements in g are observed for a silicon particle supporting only magnetic type resonances. In some embodiments, high enhancements in g are absent for a silicon particle supporting only electric type resonances. In some embodiments, the wavelength shifts between maxima in $g=g_{CPL}$ and maxima in $C=C_{CPL}$ are also observed for a silicon particle supporting only magnetic type resonances.

In some embodiments, maximum CD enhancements occur at magnetic resonances. In some embodiments, maximum dissymmetry factor enhancements occur shifted from resonances. In some embodiments, maximum dissymmetry factor enhancements occur shifted from resonances due to high electric field enhancements found on resonance.

Figure 9:
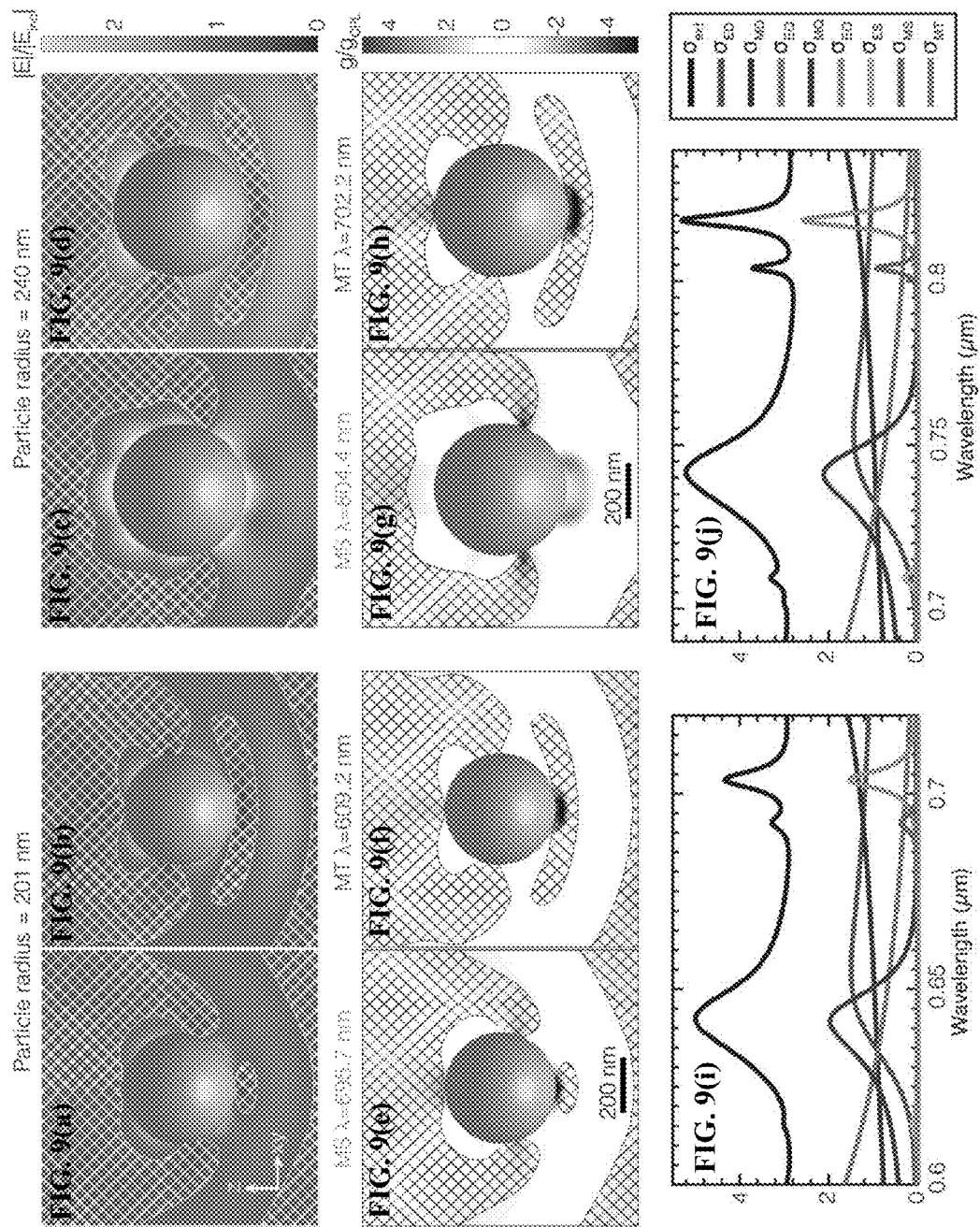
FIG. 9(a)-FIG. 9(d) show spatial distributions of electric field enhancement and FIG. 9(e)-FIG. 9(h) show spatial distributions of dissymmetry factor enhancement for nanospheres with radius 201 nm (left) and 240 nm (right).
FIG. 9(i) and FIG. 9(j) show total extinction cross-section and contributions from individual modes for nanospheres with radius 201 nm (FIGS. 9(i)) and 240 nm (FIG. 9(j)).

In FIG. 4 and FIG. 9, regions where the magnitude of the electric field (E) is less than that of the incident field ($E_{inc}$) are shown with cross-hatches. A region of negative enhancement is one in which the opposite enantiomer than the one being targeted will absorb more energy. In some embodiments, many regions of negative enhancement occur in regions where $E<E_{inc}$. In some embodiments, both enantiomers will have low absorption in regions of negative enhancement where $E<E_{inc}$. As a result, the effect of the negative enhancement region is mitigated. Therefore, in some embodiments, the overall positive enhancement for a target enantiomer is maintained. In some embodiments, the overall positive enhancement for a target enantiomer is not affected significantly. In some embodiments, the overall positive enhancement for a target enantiomer is maintained and not affected significantly.

In the positive z direction, $|\tilde{E}|<|\tilde{E}_{inc}|$ wherever there is a local maximum of negative enhancement. Therefore, even though the opposite enantiomer will absorb more light in these regions, this effect is mitigated by the lower total absorption. Therefore, the the overall positive enhancement for the target enantiomer is preserved.

In some embodiments, for MO-associated mode, regions of negative enhancement that occur where $|\tilde{E}|\geq|\tilde{E}_{inc}|$ are restricted to the negative z side of the particle. In some embodiments, for MO-associated mode, regions of negative enhancement that occur where $|\tilde{E}|\geq|\tilde{E}_{inc}|$ are restricted to the negative z side of the particle can be blocked with an index-matched substrate.

In some embodiments, for MS- and MT-associated modes, regions of negative enhancement that occur where $|\tilde{E}|\geq|\tilde{E}_{inc}|$ are not restricted to the negative z side of the particle. In some embodiments, for MS- and MT-associated modes, regions of negative enhancement that occur where $|\tilde{E}|\geq|\tilde{E}_{inc}|$ are not restricted to the negative z side of the particle and cannot be blocked with an index-matched substrate.

In some embodiments, a linear correlation exists between peak wavelength of MO-associated enhancements and radii of the silicon particles. In some embodiments, a linear correlation exists between peak wavelength of MS-associated enhancements and radii of the silicon particles. In some embodiments, a linear correlation exists between peak wavelength of MT-associated enhancements and radii of the silicon particles. In some embodiments, a linear correlation exists between peak wavelengths of MO-, and MS-associated enhancements and radii of the silicon particles. In some embodiments, a linear correlation exists between peak wavelengths of MS-, and MT-associated enhancements and radii of the silicon particles. In some embodiments, a linear correlation exists between peak wavelengths of MO-, and MT-associated enhancements and radii of the silicon particles. In some embodiments, a linear correlation exists between peak wavelengths of MO-, MS-, and MT-associated enhancements and radii of the silicon particles. In some embodiments, as peak wavelengths tracked linearly with particle size, a peak wavelength with an MO-, MS-, or MT-associated peak in $g/g_{CPL}$ can be matched to a silicon nanosphere with a particle radius, and vice versa.

Without being bound by any theory, lower g enhancement values at smaller particle sizes and shorter peak enhancement wavelengths likely occur due to losses in the material. In some embodiments, the particle is a low-loss, high-index dielectric material. In some embodiments, the low-loss, high-index dielectric material is chalcogenide glass. In some embodiments, chalcogenide glass comprises sulfur, selenium and tellurium. In some embodiments, chalcogenide glass is germanium telluride. In some embodiments, the material is Ti-based (e.g., TiO2). In some embodiments, the material is Si-based. In some embodiments, the material is metasurfaces. In some embodiments, the material is metamaterials. In some embodiments, the low-loss, high-index dielectric material provides peak enhancements of about 6-fold to about 18-fold. In some embodiments, MO peak enhancement is about 6-fold to about 18-fold. In some embodiments, MS peak enhancement is about 6-fold to about 18-fold. In some embodiments, MT peak enhancement is about 6-fold to about 18-fold. In some embodiments, the low-loss, high-index dielectric material provides peak enhancements of about 3, 6, 9, 12, 15, 18, 21, 24, 27, 30, 33, or 36-fold, within a range defined by any two of the aforementioned values.

In some embodiments, nanoparticles made of other substances are contemplated. Non-limiting examples include silver, gold, nickel, copper, titanium, silicon, galadium, palladium, platinum, or chromium, as well as including metal alloys, composites, and amalgams. Other non-limiting examples include dielectric materials, such as, lead germanium telluride and titanium dioxide. In some embodiments, the use of a combination of nanoparticles made of different substances is contemplated.

In some embodiments, in addition to inducing physical difference in charge or molecular weight can then be used to separate the racemic mixture into enantiopure solutions, other applications are also contemplated. These include, without limitations, the possibility of generating products with altered properties. For example, by selectively photoionizing or photolysing one enantiomer while leaving the other intact, it is possible to generate products with altered physical and/or chemical properties include, without limitations, absorption, boiling point, capacitance, melting point, concentration, distribution, elasticity, electric charge, electrical conductivity, electrical impedance, electric field, electric potential, flow rate, fluidity, luminance, luminescence, mass, opacity, plasticity, specific heat, resistivity, reflectivity, refractive index, volume, wave impedance, temperature, specific heat, latent heat, thermal conductivity, density, viscosity, color, smell, taste, appearance, texture, solubility, polarity, miscibility, potency, heat of combustion, enthalpy of formation, toxicity, chemical stability in a given environment, flammability, oxidation state, etc.

In some embodiments, depending on which enantiomer is to be to targeted, the same solution could be illuminated with CPL of one or the other handedness in order to selectively target one of the other enantiomer. In some embodiments, if the selective photoexcited reaction is not run to 100% completion, it is possible to amplify the resulting enantiomeric excess with an asymmetric autocatalytic method such as the Soai reaction.[6]

The following Examples are non-limiting and other exemplary variants as contemplated by one of ordinary skill in the art are acceptable.

EXAMPLES

Example 1

Determining Kuhn's Dissymmetry Factor

Kuhn's dissymmetry factor was determined near a nanoparticle illuminated by a circularly polarized plane wave (FIG. 1). A molecule in the electromagnetic field surrounding the particle will become polarized, acquiring an electric dipole moment, $\tilde{p}$, and a magnetic dipole moment, $\tilde{m}$. This response was determined by the molecule's electric polarizability, $\alpha$, magnetic polarizability, $\chi$, and chiral polarizability, $G$:

$$\tilde{p} = \alpha\tilde{E} - iGB, \tilde{m} = \chi\tilde{B} + iGE \quad (1)$$

where $\tilde{E}$ and $\tilde{B}$ are the time-independent complex electric magnetic fields, respectively.

A randomly oriented molecule's rate of absorption of incident R-CPL (+) or L-CPL (−) is given by[28]

$$A^{\pm} = \frac{\omega}{2}(\alpha|\tilde{E}|^2 + \chi''|\tilde{B}|^2) \mp \frac{2}{\varepsilon}G''C \quad (2)$$

where " denotes the imaginary component of a complex quantity and $\omega$ and $\varepsilon 0$ denote the angular frequency of light and permittivity of free space. C represents the electromagnetic density of chirality and is defined as [10,29-31]

$$C \equiv \frac{\varepsilon_0}{2}E\cdot(\nabla\times E) + \frac{1}{2\mu_0}B\cdot(\nabla\times B) = -\frac{\omega\varepsilon_0}{2}\text{Im}(\tilde{E}*\cdot\tilde{B}) \quad (3)$$

where E and B denote the time-dependent real part of the electric and magnetic fields, respectively.

For CPL in a vacuum, $$C_{CPL} = \pm\frac{\omega\varepsilon_0}{2c}E_0^2,$$

where E0 is the incident electric field amplitude. Together, the electromagnetic density of chirality and the molecule's chiral polarizability determine the CD signal of the molecule, which is proportional to the preferential absorption of R-CPL (+) and L-CPL (−):

$$CD \propto A^+ - A^- = -\frac{4}{\varepsilon_0}G''C \quad (4)$$

As seen above, any enhancement in C will be observed as an enhancement in the CD signal: $CD/CD_{CPL} = C/C_{CPL}$.

The efficiency of an enantioselective photochemical reaction is proportional to Kuhn's dissymmetry factor, g, which is defined as preferential absorption normalized to the total absorption:[28,30]

$$g \equiv \frac{2(A^+ - A^-)}{A^+ - A^-} \quad (5)$$

Plugging eq 2 into eq 5 and assuming that $\chi''|\tilde{B}|^2$ is negligibly small, as it is for most molecules, Kuhn's dissymmetry factor becomes $$g = -\left(\frac{G''}{\alpha''}\right)\left(\frac{8C}{\omega\varepsilon_0|\tilde{E}|^2}\right) \quad (6)$$

It is possible to separate the expression for g into one factor that contains only inherent properties of the chiral molecule and another factor that contains only properties of the electromagnetic field, which can be manipulated by changing the environment of the molecule. Therefore, by manipulating the fields, it is possible to enhance the dissymmetry factor for any chiral molecule. It is useful to note that, for CPL, $g_{CPL} = -4G''/c\alpha''$. Therefore, eq 6 can be rewritten as $$g = g_{CPL}\frac{2c}{\omega\varepsilon_0}\frac{C}{|\tilde{E}|^2} \quad (7)$$

g describes the preferential absorption of a chiral enantiomer in a racemic solution (FIG. 2).

The maximum value of g is 2, since one enantiomer cannot absorb more than 100% of the incident light. However, this maximum value is not reached by CPL excitation since G" is very small for most molecules.

Example 2

Increasing Kuhn's Dissymmetry Factor

Kuhn's dissymmetry factor (g) can be increased above $g_{CPL}$ either by increasing the local density of chirality or by decreasing the electric field intensity. In all existing schemes to enhance g, field intensities are decreased. In these cases, both enantiomers absorb very little light, leading to less efficient photolysis or photoionization of the molecules. Ideally, the dissymmetry factor would instead be enhanced by increasing the local density of chirality while not decreasing the total field intensity.

To achieve enhanced C without decreasing the electric field magnitude $|\tilde{E}|$, coexisting electric and magnetic resonances that are in phase result in spatially averaged enhancements of C, due to the fact that C involves the dot product of both $\tilde{E}^*$ and $\tilde{B}$.[31]

Example 3

Nanospheres to Enhance Kuhn's Dissymmetry Factor

While several optical antennas support electric and magnetic resonances,[32-35] silicon nanospheres present both a simple and computationally tractable system to elucidate the requirements to enhance g. Though geometrically achiral, the nanospheres nevertheless support electric and magnetic Mie resonances[36] that can control the polarization of light both in the near-field and far-field radiation regimes.[37] Thus, in some embodiments, silicon nanospheres were explored as a platform to enhance the enantioselective interaction between CPL and chiral molecules.

A silicon sphere[38] with a radius of 436 nm in a material with a background index of 1 was considered. Mie theory[39] was used to calculate local electric and magnetic fields near the silicon nanosphere. The extinction spectrum was plotted in FIG. 3(a). A particle of this size supports a dipolar magnetic mode (MD) at 3.1 μm, dipolar electric mode (ED) at 2.4 μm, and higher-order modes up to a 32nd electric pole (ET) at 1.2 μm, as labeled in FIG. 3(a). Even higher-order modes exist at shorter wavelengths, but the study was restricted to 1-3.5 μm to match vibrational modes of typical chiral molecules for photolysis[40] and minimize materials loss.

Example 4

Spatial Maxima Plots

FIG. 3(b) and FIG. 3(c) plot the spatial maxima of the CD enhancement, $C/C_{CPL}$, and the enhanced dissymmetry factor, $g/g_{CPL}$ at each wavelength. In FIG. 3(c), spatial locations are only included where the magnitude of the total electric field is greater than that of the incident field to ensure that total molecular absorption remains at least equal to CPL in free space. Thus, the enhancements of g can be directly attributed to enhancements of C. The maxima of $C/C_{CPL}$ and $g/g_{CPL}$ occur at wavelengths closely corresponding to magnetic resonances. Further, peak values of $C/C_{CPL}$ are highest at higher-order modes. For instance, C is enhanced 33-fold at λ=1684.5 nm near the magnetic octopole (MO) resonance, 78-fold at λ=1390.0 nm near the magnetic 16-pole (MS) resonance, and 169-fold at λ=1192.8 nm near the magnetic 32-pole (MT) resonance. Similarly, g is enhanced 4-fold at λ=1690.7 nm, 7-fold at λ=1391.82 nm, and 7-fold at λ=1193.4 nm, near the MO, MS, and MT resonances, respectively. Maxima of $g/g_{CPL}$ are shifted from maxima of $C/C_{CPL}$ and the magnetic resonances by a few nanometers due to high electric field enhancements found on resonance, which depress the enhancement of g.

Example 5

Enhancement of Kuhn's Dissymmetry Factor Based on Order of Magnetic Mode

As shown in FIG. 3(a)-FIG. 3(c), lower-order magnetic modes are associated with lower enhancements in g, and the corresponding peaks in $g/g_{CPL}$ have broader line widths. For example, the MO-associated peak in $g/_{am}$ is characterized by a full-width at half-maximum (fwhm) of 20 nm, while achieving a dissymmetry factor 4 times larger than CPL. This line width is wider than the peak widths of the MS- and MT-associated peaks, which have fwhm's of 3 and 2 nm, respectively. However, the MS- and MT-associated enhancements in g are higher at roughly 7 times larger than CPL. Therefore, excitation of the lower-order modes is more tolerable to differing excitation wavelengths and sphere sizes, while the excitation of higher-order modes provides more efficient preferential absorption.

Example 6

Spatial Distributions of the MO-, MS-, and MT-Associated Enhancements

The spatial distributions of the MO-, MS-, and MT-associated enhancements of total electric field, CD signal, and the dissymmetry factor are shown in FIG. 4(a)-FIG. 4(l). Because the maxima of $C/C_{CPL}$ are wavelength-shifted from maxima of $g/_{CPL}$, the field enhancement was plotted at both the peak wavelengths for $C/C_{CPL}$ (FIG. 4(a)-FIG. 4(c)) and the peak wavelengths for $g/g_{CPL}$ (FIG. 4(g)-FIG. 4(i)). The small wavelength shift was attributed to the fact that peak wavelengths for $C/C_{CPL}$ occur closer to peak magnetic resonance wavelengths, leading to larger field enhancements (FIG. 4(d)-FIG. 4(f)) compared to the smaller field enhancements (FIG. 4(g)-FIG. 4(i)) found at peak wavelengths for $g/g_{CPL}$.

Example 7

Electric and Magnetic Contributions to Enhancement of g

The Mie expansion of a scattered electromagnetic field in vector spherical harmonics takes the form[5]

$$E_{scat} = \sum_{n=1}^{\infty} E_n(ia_n N_{eln}^{(3)} - b_n M_{oln}^{(3)}), \quad H_{scat} = \frac{k}{\omega\mu}\sum_{n=1}^{\infty} E_n(ib_n N_{oln}^{(3)} + a_n M_{eln}^{(3)}) \quad (8)$$

where the scattering coefficients $a_n$ correspond to electric type resonances and $b_N$, to magnetic type resonances, M and N are the vector spherical harmonics and $$E_n = i^n E_0 \frac{2n+1}{n(n+1)} \quad (9)$$

Figure 5:
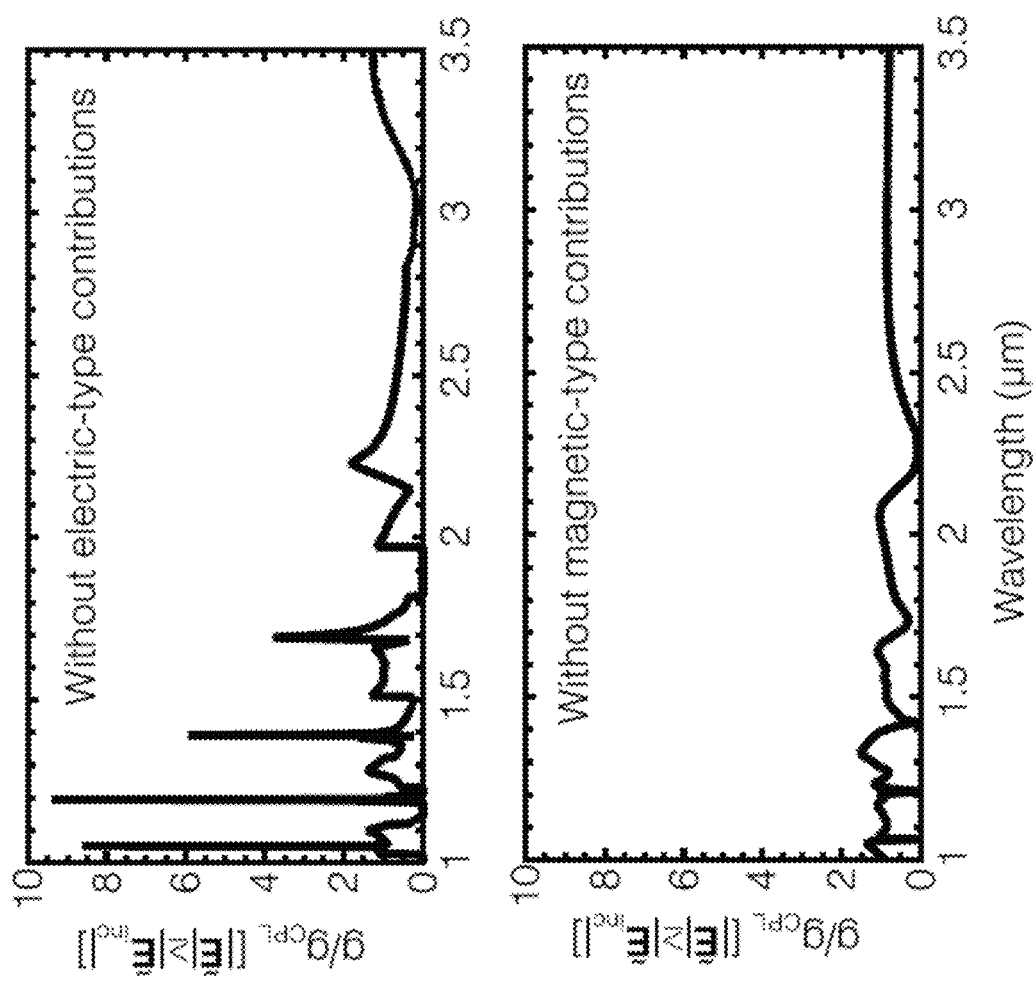
FIG. 5 shows that magnetic-type resonances are necessary for dissymmetry factor enhancements where the electric field enhancement is at least 1.

To determine the necessity of the contributions from magnetic resonances, we modify the calculation for the dissymmetry factor enhancement, $g=g_{CPL}$ near a silicon sphere of radius 436 nm illuminated by CPL as follows. First, the electric coefficients $a_n$ was set to zero and calculated the resulting enhancement in g, shown in FIG. 5 (top). Next, the magnetic coefficients $b_n$ was sent to zero and the resulting enhancement in g was calculated, shown in of FIG. 5 (bottom). The high enhancements observed for a silicon particle supporting both magnetic and electric resonances were present in a particle supporting only magnetic type resonances, but were absent in a particle supporting only electric type resonances. Therefore, strong magnetic type resonances are a necessary condition for enhancing g in regions where $|\tilde{E}| \geq |\tilde{E}_{inc}|$. The wavelength shifts between maxima in $g=g_{CPL}$ and maxima in $C=C_{CPL}$ are also observed in the case without electric-type contributions.

Example 8

Spatial Distributions of Electric Field, CD, and Dissymmetry Factor Enhancements for a Silicon Nanosphere The MO-associated peak in $g/g_{CPL}$ is the first higher-order peak exhibiting an enhancement greater than 3-fold. FIG. 4(a) shows the field distribution for the MO-associated field enhancement has six local maxima in the near-field of the nanosphere. Within the first 100 nm of the nanosphere surface, $|\tilde{E}| \geq |\tilde{E}_{inc}|$ due to the field enhancement caused by the resonance of the nanosphere. The corresponding spatial plot for $g/g_{CPL}$ (FIG. 4(j)) shows that local positive and negative peaks occur at latitudes on the nanosphere spaced directly between the six local maxima in $|\tilde{E}|$. Similar trends follow in the MS- and MT-associated enhancements. In all three cases, the enhanced field in the vicinity of the particle leads to enhancements of the dissymmetry factor while maintaining field strengths greater than or equal to incident field strengths. Additionally, nearby field hot spots are at most 5 times higher rather than 40 times higher as is the case for the elliptical standing wave system.[30] Therefore, molecules located in nearby field hot spots around the silicon nanospheres are more likely to be preserved rather than destroyed.

Conversely, molecules located in regions where $|\tilde{E}| < |\tilde{E}_{inc}|$ (cross-hatched regions of FIG. 4) will have a lower total absorption compared to illumination with CPL. In these regions, even if the dissymmetry factor is high, the separation efficiency is lower. Cross-hatched regions in FIG. 4(g)-FIG. 4(l) exhibit electric field strength $|\tilde{E}|$ lower than the incident field strength and are excluded from the optimization.

Example 9

Relationship Between Silicon Particle Radii and Spectral Position of Peak Enhancements By tuning the radii of the silicon particles, the spectral positions of the three MO-, MS-, and MT-associated peak enhancements across particle size were tracked (FIG. 6). Peak wavelengths tracked linearly with particle size, allowing tuning of the resonances of the nanosphere to match various molecular resonances. As an example of the chemical relevance of spectral position of peak enhancements, limonene exhibits a vibrational CD peak (i.e., peak wavelength—y axis in FIG. 6) at 3.425 μm.[41] To match the peak wavelength of 3.425 μm with an MO-associated peak in $g/g_{CPL}$, a silicon nanosphere with a particle radius (x axis in FIG. 6) of 893 nm is used, which will provide a peak enhancement of 4-fold.

In order to achieve selective photodestruction, vibrational resonances can be selectively excited, resulting in bond dissociation. For example, limonene has a vibrational resonance at 3.42 μm with a lifetime on the order of 0.1 ps. Absorption of ~10 photons are needed in order to break a 3.7eV C-C bond. The silicon Dolmen structure targets this vibrational resonance (Example 16).

Example 10

Relationship Between Silicon Particle Radii and Enhancements of Dissymmetry Factor For nanospheres with radii ranging from 150 to 450 nm, enhancements in g improve with particle radius, r, before saturating to a maximum value. The MO-associated peak (top line in FIG. 7) reaches a maximum of 4.5 and saturates around r=270 nm, the MS-associated peak (middle line in FIG. 7) reaches a maximum of 6.85 and saturates around r=300 nm, and the MT-associated peak (bottom line in FIG. 7) reaches a maximum of 6.9 and saturates around r=436 nm.

Notably, local minima in MS and MT data are due to the maximum region of enhancement transferring from one spatial local maximum in $g/g_{CPL}$ to another as the particle size increases.

Example 11

Resonance Effects on the Enhancement of g

Figure 8:
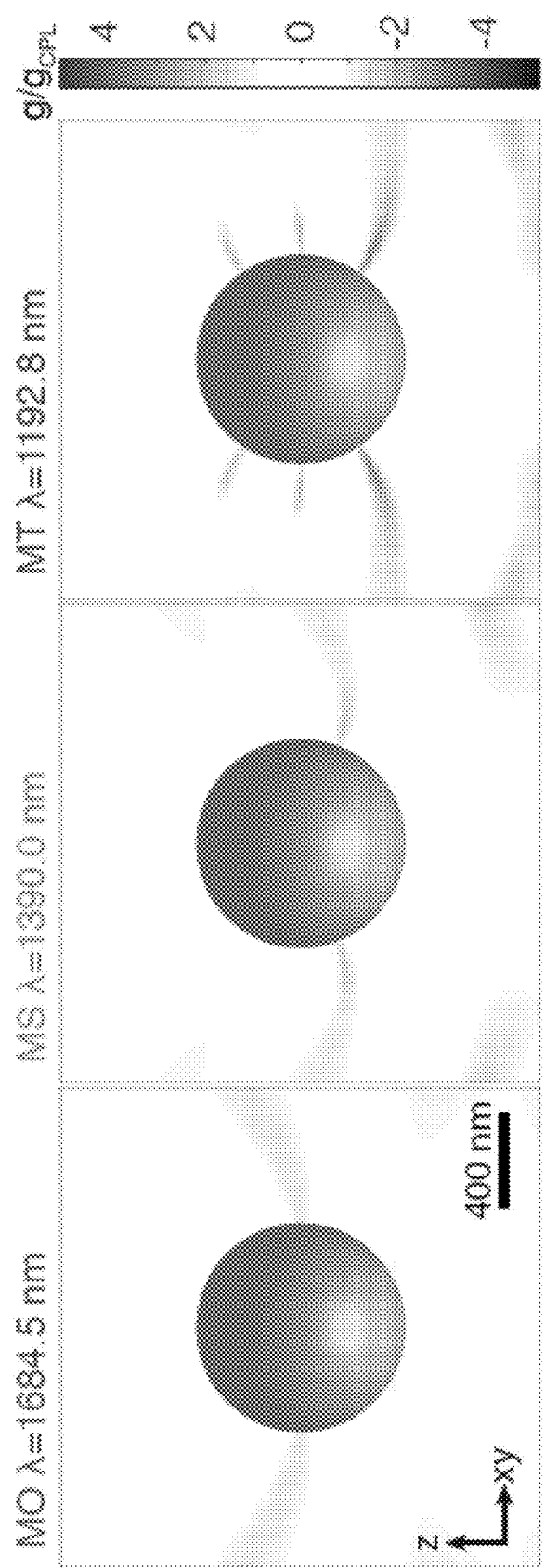
FIG. 8 shows spatial distribution of dissymmetry factor enhancement at wavelengths of λ=1684.5 nm, 1390.0 nm, and 1192.8 nm, from left to right.

FIG. 8 shows a plot of $g=g_{CPL}$ at peak wavelengths for $C=C_{CPL}$. The electric field strengths due to resonances were high enough to decrease the value of $g=g_{CPL}$, leading to a wavelength shift between maxima for $C=C_{CPL}$ and maxima for $g=g_{CPL}$.

Higher order modes were less dominant features in smaller nanospheres. At these shorter wavelengths where materials loss is more prevalent, electric field profiles were dominated by a mixture of lower order modes (MS and MT contributions in FIG. 9(i) and MT contribution in FIG. 9(j)) and did not exhibit a clear field profile associated with a MS or MT mode (FIG. 9(a), FIG. 9(b), FIG. 9(d)).

As a result, local spatial maxima in $g=g_{CPL}$ occurred in different locations as compared to particles as large as 436 nm (FIG. 9(e), FIG. 9(j), FIG. 9(h)). When the particle was large enough to support a dominant higher order magnetic mode (FIG. 9C), MS contribution in FIG. 9(j)), local maxima in $g=g_{CPL}$ moved to locations similar to larger particles. The emergence of higher order modes and subsequent migration of maxima in $g=g_{CPL}$ was likely the cause of variations in MS- and MT-associated peak enhancement values before saturation as shown in FIG. 7.

Example 12

Material Losses

Lower g enhancement values at smaller particle sizes and shorter peak enhancement wavelengths likely occur due to losses in the material. Material loss in silicon at wavelengths below 1100 nm (shown as curved line in FIG. 6) decrease peak dissymmetry factor enhancements (dashed lines in FIG. 6 and FIG. 7). FIG. 6 shows losses in silicon become negligible for wavelengths longer than λ=1100 nm. Accordingly, g increased with particle size until a resonance peak occurs at a wavelength longer than 1100 nm, at which the associated enhancement in g reached a maximum value as seen by comparing FIG. 6 and FIG. 7. A low-loss, high-index dielectric material could provide greater enhancements. For instance, with n=6 (typical for chalcogenide glasses such as lead germanium telluride[42-44]), the MO, MS, and MT peak enhancements in g were increased to 7.8-, 7.5-, and 10-fold, respectively. Similar enhancements were seen for TiO2 at visible wavelengths, which exhibited a lower index than Si, but lower loss. Alternatively, metasurfaces and metamaterials could be used to achieve even higher effective refractive indices.[45-49]

Example 13

Localization of Positive Enhancements in Dissymmetry Factor

The largest positive enhancements in g occur at the surface of the nanosphere. To demonstrate enhancements for molecules located near the 436 nm radius nanosphere, the radially averaged enhancements of g up to 100 nm from the nanosphere surface for the MS-associated enhancement was plotted (FIG. 10 (inset)).

Figure 10:
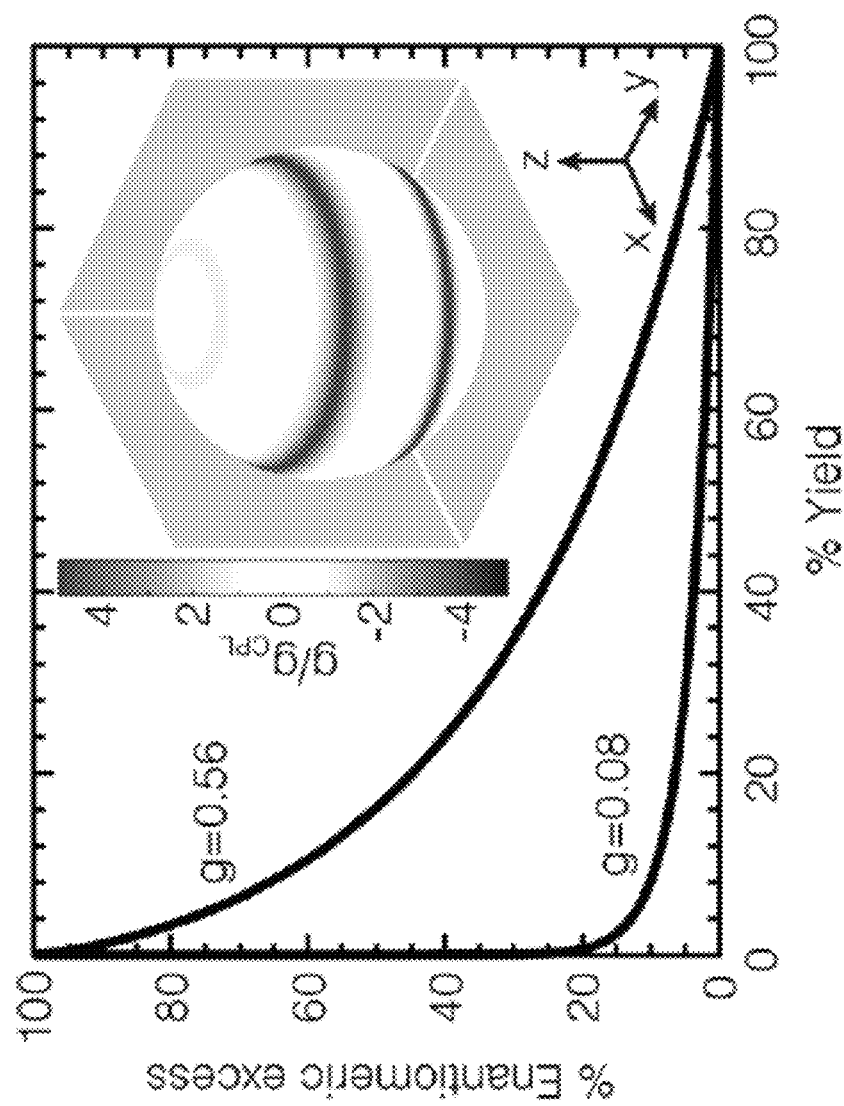
FIG. 10 shows enantiomeric excess achievable for a given extent of reaction.

Enantiomeric excess achievable for a given extent of reaction increased dramatically when g was increased (FIG. 10). Spatial distribution of dissymmetry factor enhancement at λ=1391.82 nm is shown in FIG. 10 (inset). $g/g_{CPL}$ was radially averaged within 100 nm of the nanosphere surface and displayed on a unit sphere. Due to the axial symmetry of the system, regions of high enhancement in CD signal and dissymmetry factor occurred as spatial rings. Regions of high enhancement of g near the equator of the nanosphere resulted in large spatial extents of enhancement due to the axial symmetry of the system. With a 7-fold enhancement in dissymmetry factor, a 20% enantiomeric excess could be reached with a yield of 50% instead of 1%.

Example 14

Localization of Positive Enhancements in Dissymmetry Factor

To determine the impact of the achievable enhancements of the dissymmetry factor on a light-driven separation process, FIG. 10 compared the necessary reaction yield for a molecule with g=0.08 such as camphor to the reaction yield for the silicon nanosphere-enhanced case. The 7-fold enhancement in g herein increased the dissymmetry factor of camphor to g=0.56, which was within the upper limit of g≤2. This enhanced value of allowed a separation of camphor as presented by Kagan et al.[9] to reach 20% enantiomeric excess with 50% yield instead of 1%.

Example 15

Calculation of Separation Efficiency

To determine the impact that enhancing the dissymmetry factor by a factor of 7 would have on a selective photochemical reaction, we calculate the achievable enantiomeric excess (EE) for a given extent of reaction in FIG. 10. We use the following relation, as formulated by Kagan et. al.[51]

$$x = 1 - \frac{1}{2}\left[\left(\frac{1+y}{1-y}\right)^{1/2-1/g} + \left(\frac{1+y}{1-y}\right)^{-1/2-1/g}\right] \qquad (10)$$

where x is the extent of the reaction and y is the EE. Note that the yield of the reaction is 1−x. We use camphor as a reference molecule with base value of g=0:08. To achieve an EE of 20%, the reaction needs to be run to 99% completion, giving a product yield only 1%. A 7-fold enhancement in g would achieve an EE of 20% when the reaction is run to 50% completion, giving a product yield of 50%, a 50-fold improvement compared to using CPL alone.

Several factors were not taken into account in this simplified analysis of separation efficiency. First, the duration of any reaction would depend on several environmental factors such as temperature, concentration, and choice of target molecules. Second, the electric field strength was also not constant throughout space as it was in the experiment of Kagan et. al.[2] Specifically, the electric field was at lower strength in many regions where negative enhancement occurs (FIG. 4). Therefore, a full analysis of separation efficiency requires a calculation taking these additional factors into account.

Example 16

Comparison Between Silver Sphere and Silicon Sphere

Enantiomers are pairs of chiral molecules that are non-superimposable mirror images of each other. Enantiomers serve different biological and chemical functions due to their differing structures. Thus, separation of opposite enantiomers is of critical importance. Confirmation of enantiopure products is of equal importance and is accomplished via CD spectroscopy. However, the sensitivity of CD spectroscopy is limited and requires high sample concentrations. Chiral light provides a platform for differentiating between enantiomers. The effective chirality of light can be increased beyond that of CPL. By enhancing C, the signal of CD spectroscopy measurements can be boosted. By enhancing g, selective photodestruction of enantiomers can be achieved.

For example, A l0nm radius silver sphere excited by CPL shows only local enhancement of C at λ=359nm. In contrast, a 75nm radius silicon sphere shows global enhancement of C due to concurrent electric and magnetic dipoles at λ=625nm. Near fields were calculated using Mie theory[39], agreeing with analogous calculations using the Boundary Element Method[37].

A 10 nm silver sphere shows local enhancement of g, but restricted to a small spatial region at λ=368nm. In contrast, in a 75 nm silicon sphere, interference between the electric and magnetic dipoles results in strong backscattering at λ=564nm, and backscattered light interferes with incident light, leading to several local regions of enhanced g. Interference between higher order modes in a silicon Dolmen structure results in local enhancement of g at λ=3.51μm.

Thus, combined electric and magnetic dipoles are key to achieving global enhancement of CD spectroscopy signals, and deconstructive interference between electric and magnetic dipoles in silicon spheres and higher order modes in Dolmen structures allow for selective photodestruction of enantiomers.

Combined electric and magnetic dipoles are key to achieving global enhancement of CD spectroscopy signals. Additionally, deconstructive interference between electric and magnetic dipoles in silicon spheres and higher order modes in Dolmen structures are a promising route to reaching selective photodestruction of enantiomers.

Example 17

Camphor

An optical nanostructure is designed, synthesized and characterized according to the present disclosure. The nanostructure comprises nanomaterial, metamaterial, or a combination thereof. After optimizing the nanostructure, selective photoionization and/or photolysis is performed by immersing the nanostructure in a solution of a racemic mixture of camphor, whose optical separation characteristics have previously been well-documented. [4] Thereafter, enantiomeric excess is determined using CD spectroscopy. The nanostructure used is designed such that an increase in enantiomeric excess achieved is at least 7 times greater than that achieved with CPL alone. For camphor, the nanostructures enables about 20% enantiomeric excess with a yield of about 50%, instead of 1% as achieved with CPL alone.[9] The nanostructure design is optimized further to achieve even greater enhancements in obtaining enantiomeric excess.

Example 18

Applicability in Pharmaceutical Industry—1

The purification of racemic solutions is critical in a variety of disciplines, especially molecular synthesis, drug discovery, and agriculture. In the pharmaceutical industry, the efficacies of chiral drugs are often affected by the presence of the opposite enantiomer.[1] For example, one enantiomer of Ethambutol treats tuberculosis while the other causes blindness. An optical nanostructure is designed, synthesized and characterized according to the present disclosure. The nanostructure comprises nanomaterial, metamaterial or a combination thereof.

After optimizing the nanostructure, selective photoionization and/or photolysis is performed by immersing the nanostructure in a solution of a racemic mixture of Ethambutol. Thereafter, enantiomeric excess is determined using CD spectroscopy. The nanostructure used is designed such that an increase in enantiomeric excess achieved for Ethambutol is at least 7 times greater than that achieved with CPL alone.

Example 19

Applicability in Pharmaceutical Industry—2

The purification of racemic solutions is critical in a variety of disciplines, especially molecular synthesis, drug discovery, and agriculture. In the pharmaceutical industry, the efficacies of chiral drugs are often affected by the presence of the opposite enantiomer.[1] For example, one enantiomer of the antidepressant Prozac induces cardiac arrhythmia.[53]

An optical nanostructure is designed, synthesized and characterized according to the present disclosure. The nanostructure comprises nanomaterial, metamaterial or a combination thereof. After optimizing the nanostructure, selective photoionization and/or photolysis is performed by immersing the nanostructure in a solution of a racemic mixture of Prozac. Thereafter, enantiomeric excess is determined using CD spectroscopy. The nanostructure used is designed such that an increase in enantiomeric excess achieved for Prozac is at least 7 times greater than that achieved with CPL alone.

Example 20

Applicability in Pharmaceutical Industry—3

The purification of racemic solutions is critical in a variety of disciplines, especially molecular synthesis, drug discovery, and agriculture. In the pharmaceutical industry, the efficacies of chiral drugs are often affected by the presence of the opposite enantiomer.[1] For example, pain relief begins within twelve minutes of using enantiopure Ibuprofen rather than in thirty minutes when using a racemic mixture of Ibuprofen.[53]

An optical nanostructure is designed, synthesized and characterized according to the present disclosure. The nanostructure comprises nanomaterial, metamaterial or a combination thereof. After optimizing the nanostructure, selective photoionization and/or photolysis is performed by immersing the nanostructure in a solution of a racemic mixture of Ibuprofen. Thereafter, enantiomeric excess is determined using CD spectroscopy. The nanostructure used is designed such that an increase in enantiomeric excess achieved for Ibuprofen is at least 7 times greater than that achieved with CPL alone.

Example 21

Seractil (Ibuprofen)

Seractil is an FDA approved drug. Since the clinical trials have already been performed for Seractil, developing a cost-effective separation method would increase its availability and efficacy. An optical nanostructure is designed, synthesized and characterized according to the present disclosure. The nanostructure comprises nanomaterial and metamaterial. After optimizing the nanostructure, selective photoionization and/or photolysis is performed by immersing the nanostructure in a solution of a racemic mixture of Seractil. Thereafter, enantiomeric excess is determined using CD spectroscopy. The nanostructure used is designed such that an increase in enantiomeric excess achieved for Seractil is at least 7 times greater than that achieved with CPL alone.

Example 22

Focalin (Ritalin)

Focalin is an FDA approved drug. Since the clinical trials have already been performed for Focalin, developing a cost-effective separation method would increase its availability and efficacy. An optical nanostructure is designed, synthesized and characterized according to the present disclosure. The nanostructure comprises nanomaterial and metamaterial. After optimizing the nanostructure, selective photoionization and/or photolysis is performed by immersing the nanostructure in a solution of a racemic mixture of Focalin. Thereafter, enantiomeric excess is determined using CD spectroscopy. The nanostructure used is designed such that an increase in enantiomeric excess achieved is at least 7 times greater than that achieved with CPL alone.

Example 23

Nexium

Nexium is an FDA approved drug. Since the clinical trials have already been performed for Nexium, developing a cost-effective separation method would increase its availability and efficacy. An optical nanostructure is designed, synthesized and characterized according to the present disclosure. The nanostructure comprises nanomaterial and metamaterial. After optimizing the nanostructure, selective photoionization and/or photolysis is performed by immersing the nanostructure in a solution of a racemic mixture of Nexium. Thereafter, enantiomeric excess is determined using CD spectroscopy. The nanostructure used is designed such that an increase in enantiomeric excess achieved is at least 7 times greater than that achieved with CPL alone.

Example 24

Applicability in Agricultural Industry

The purification of racemic solutions is critical in a variety of disciplines, especially molecular synthesis, drug discovery, and agriculture. In the agriculture industry, the presence of the opposite enantiomer reduces the efficacy and/or increases the toxicity of herbicides and insecticides (e.g., mecoprop and bifenthrin). In some cases, one enantiomer is often more prone to leaving residues in soil, leading to higher levels chemical pollution.[54] Currently, more than 30% of agrochemicals are chiral. For each of these molecules, companies must make a choice between developing an enantiopure solutions or selling the mixture. Unfortunately, the economic and time burden means more than 90% of chiral products are sold as racemates,[1] despite their environmental impact.

An optical nanostructure is designed, synthesized and characterized according to the present disclosure. The nanostructure comprises nanomaterial, metamaterial or a combination thereof. After optimizing the nanostructure, selective photoionization and/or photolysis is performed by immersing the nanostructure in a solution of a racemic mixture of the herbicides and insecticides. Thereafter, enantiomeric excess is determined using CD spectroscopy. The nanostructure used is designed such that an increase in enantiomeric excess achieved of the herbicides and insecticides is at least 7 times greater than that achieved with CPL alone.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

It should be understood, however, that this detailed description, while indicating preferred embodiments of the disclosure, is given by way of illustration only, since various changes and modifications within the spirit and scope of the disclosure will become apparent to those skilled in the art.

REFERENCES

The references cited in this disclosure are incorporated herein in their entireties by reference.

(1) Nguyen, L. A.; He, H.; Pham-Huy, C. Chiral drugs: an overview. *Int. J. Biomed. Sci.* 2006, 2, 85-100.

(2) Development of New Stereoisomeric Drugs. 1992; http://www.fda.gov/Drugs/GuidanceComplianceRegulatoryInformation/Guidances/ucm1228 83.htm, accessed 09-03-2016.

(3) Ahuja, S.; Scypinski, S. *Handbook of Modern Pharmaceutical Analysis*; Academic Press, 2010.

(4) Ahuja, S. *Chiral Separation Methods for Pharmaceutical and Biotechnological Products*; John Wiley & Sons, 2011.

(5) Zhdanov, D. V.; Zadkov, V. N. Absolute asymmetric synthesis from an isotropic racemic mixture of chiral molecules with the help of their laser orientation-dependent selection. *J. Chem. Phys.* 2007, 127, 244312.

(6) Feringa, B. L.; van Delden, R. A. Absolute Asymmetric Synthesis: The Origin, Control, and Amplification of Chirality. *Angew. Chem., Int. Ed.* 1999, 38, 3418-3438.

(7) Modica, P.; Meinert, C.; de Marcellus, P.; Nahon, L.; Meierhenrich, U. J.; Le Sergeant d'Hendecourt, L. Enantiomeric Excesses Induced in Amino Acids by Ultraviolet Circularly Polarized Light Irradiation of Extraterrestrial Ice Analogs: a Possible Source of Aymmetry for Prebiotic Chemistry. *Astrophys. J.* 2014, 788, 79.

(8) Kagan, H. B.; Balavoine, G.; Moradpour, A. Can circularly polarized light be used to obtain chiral compounds of high optical purity? *J. Mol. Evol.* 1974, 4, 41-48.

(9) Balavoine, G.; Moradpour, A.; Kagan, H. B. Preparation of chiral compounds with high optical purity by irradiation with circularly polarized light, a model reaction for the prebiotic generation of optical activity. *J. Am. Chem. Soc.* 1974, 96, 5152-5158.

(10) Tang, Y.; Cohen, A. E. Enhanced enantioselectivity in excitation of chiral molecules by superchiral light. *Science* 2011, 332, 333-336.

(11) Choi, J. S.; Cho, M. Limitations of a superchiral field. *Phys. Rev. A: At., Mol., Opt. Phys.* 2012, 86, 063834.

(12) Schaferling, M.; Yin, X.; Engheta, N.; Giessen, H. Helical Plasmonic Nanostructures as Prototypical Chiral Near-Field Sources. *ACS Photonics* 2014, 1, 530-537.

(13) Ferry, V. E.; Hentschel, M.; Alivisatos, A. P. Circular Dichroism in Off-Resonantly Coupled Plasmonic Nanosystems. *Nano Lett.* 2015, 15, 8336-8341.

(14) Duan, X.; Kamin, S.; Sterl, F.; Giessen, H.; Liu, N. Hydrogen-Regulated Chiral Nanoplasmonics. *Nano Lett.* 2016, 16, 1462-1466.

(15) Lu, F.; Tian, Y.; Liu, M.; Su, D.; Zhang, H.; Govorov, A. O.; Gang, 0. Discrete Nanocubes as Plasmonic Reporters of Molecular Chirality. *Nano Lett.* 2013, 13, 3145-3151.

(16) Alizadeh, M. H.; Reinhard, B. M. Plasmonically Enhanced Chiral Optical Fields and Forces in Achiral Split Ring Resonators. *ACS Photonics* 2015, 2, 361-368.

(17) Esposito, M.; Tasco, V.; Cuscuna, M.; Todisco, F.; Benedetti, A.; Tarantini, I.; Giorgi, M. D.; Sanvitto, D.; Passaseo, A. Nanoscale 3D Chiral Plasmonic Helices with Circular Dichroism at Visible Frequencies. *ACS Photonics* 2015, 2, 105-114.

(18) Tang, Y.; Sun, L.; Cohen, A. E. Chiroptical hot spots in twisted nanowire plasmonic oscillators. *Appl. Phys. Lett.* 2013, 102, 043103.

(19) Hendry, E.; Carpy, T.; Johnston, J.; Popland, M.; Mikhaylovskiy, R. V.; Lapthorn, A. J.; Kelly, S. M.; Barron, L. D.; Gadegaard, N.; Kadodwala, M. Ultrasensitive detection and characterization of biomolecules using superchiral fields. Nat. Nanotechnol. 2010, 5, 783-787.

(20) Zhao, Y.; Saleh, A. A. E.; Dionne, J. A. Enantioselective Optical Trapping of Chiral Nanoparticles with Plasmonic Tweezers. ACS Photonics 2016, 3, 304-309.

(21) Wang, S. B.; Chan, C. T. Lateral optical force on chiral particles near a surface. Nat. Commun. 2014, 5, 10.1038/ncomms4307

(22) Rodríguez-Fortuño, F. J.; Engheta, N.; Martinez, A.; Zayats, A. V. Lateral forces on circularly polarizable particles near a surface. Nat. Commun. 2015, 6, 8799.

(23) Canaguier-Durand, A.; Hutchison, J. A.; Genet, C.; Ebbesen, T. W. Mechanical separation of chiral dipoles by chiral light. New J. Phys. 2013, 15, 123037.

(24) Hayat, A.; Mueller, J. P. B.; Capasso, F. Lateral chirality-sorting optical forces. Proc. Natl. Acad. Sci. U. S. A. 2015, 112, 13190-13194.

(25) Tkachenko, G.; Brasselet, E. Optofluidic sorting of material chirality by chiral light. Nat. Commun. 2014, 5, 3577.

(26) Cameron, R. P.; Barnett, S. M.; Yao, A. M. Discriminatory optical force for chiral molecules. New J. Phys. 2014, 16, 013020.

(27) Schaferling, M.; Dregely, D.; Hentschel, M.; Giessen, H. Tailoring Enhanced Optical Chirality: Design Principles for Chiral Plasmonic Nanostructures. Phys. Rev. X 2012, 2, 031010.

(28) Barron, L. D. Molecular Light Scattering and Optical Activity; Cambridge University Press, 2009.

(29) Lipkin, D. M. Existence of a New Conservation Law in Electromagnetic Theory. J. Math. Phys. 1964, 5, 696-700.

(30) Tang, Y.; Cohen, A. E. Optical Chirality and Its Interaction with Matter. Phys. Rev. Lett. 2010, 104, 163901.

(31) García-Etxarri, A.; Dionne, J. A. Surface-enhanced circular dichroism spectroscopy mediated by nonchiral nanoantennas. Phys. Rev. B: Condens. Matter Mater. Phys. 2013, 87, 235409.

(32) Bakker, R. M.; Permyakov, D.; Yu, Y. F.; Markovich, D.; Paniagua-Domínguez, R.; Gonzaga, L.; Samusev, A.; Kivshar, Y.; Luk'yanchuk, B.; Kuznetsov, A. I. Magnetic and electric hotspots with silicon nanodimers. Nano Lett. 2015, 15, 2137-2142.

(33) Zhou, J.; Koschny, T.; Kafesaki, M.; Economou, E. N.; Pendry, J. B.; Soukoulis, C. M. Saturation of the magnetic response of split-ring resonators at optical frequencies. Phys. Rev. Lett. 2005, 95, 223902.

(34) Fan, J. A.; Wu, C.; Bao, K.; Bao, J.; Bardhan, R.; Halas, N. J.; Manoharan, V. N.; Nordlander, P.; Shvets, G.; Capasso, F. Selfassembled plasmonic nanoparticle clusters. Science 2010, 328, 1135-1138.

(35) Wen, F.; Ye, J.; Liu, N.; Van Dorpe, P.; Nordlander, P.; Halas, N. J. Plasmon transmutation: inducing new modes in nanoclusters by adding dielectric nanoparticles. Nano Lett. 2012, 12, 5020-5026.

(36) Garcia-Etxarri, A.; Gomez-Medina, R.; Froufe-Pérez, L. S.; Lopez, C.; Chantada, L.; Scheffold, F.; Aizpurua, J.; Nieto-Vesperinas, M.; Sáenz, J. J. Strong magnetic response of submicron Silicon particles in the infrared. Opt. Express 2011, 19, 4815-4826.

(37) Garcia-Etxarri, A. Polarization singularities on high index nanoparticles. 2016, arXiv : 1207 .0016.

(38) Palik, E. D. Handbook of Optical Constants of Solids; Academic Press, 1998; Vol. 3.

(39) Bohren, C. F.; Huffman, D. R. Absorption and Scattering of Light by Small Particles; John Wiley & Sons, 2008.

(40) Stephens, P. J.; Devlin, F. J.; Pan, J.-J. The determination of the absolute configurations of chiral molecules using vibrational circular dichroism (VCD) spectroscopy. Chirality 2008, 20, 643-663.

(41) Rhee, H.; June, Y.-G.; Lee, J.-S.; Lee, K.-K.; Ha, J.-H.; Kim, Z. H.; Jeon, S.-J.; Cho, M. Femtosecond characterization of vibrational optical activity of chiral molecules. Nature 2009, 458, 310-313.

(42) Weiting, F.; Yixun, Y. Temperature effects on the refractive index of lead telluride and zinc selenide. Infrared Phys. 1990, 30, 371-373.

(43) Li, B.; Xie, P.; Zhang, S.; Liu, D. Lead germanium telluride: a mechanically robust infrared high-index layer. J. Mater. Sci. 2011, 46, 4000-4004.

(44) Li, B.; Jiang, J.; Zhang, S.-Y.; Zhang, F.-S. Low-temperature dependence of midinfrared optical constants of lead—germaniumtelluride thin film. J. Appl. Phys. 2002, 91, 3556-3561.

(45) Wei, X.; Shi, H.; Dong, X.; Lu, Y.; Du, C. A high refractive index metamaterial at visible frequencies formed by stacked cut-wire plasmonic structures. Appl. Phys. Lett. 2010, 97, 011904.

(46) Sainidou, R.; García de Abajo, F. J. Plasmon guided modes in nanoparticle metamaterials. Opt. Express 2008, 16, 4499-4506.

(47) Choi, M.; Lee, S. H.; Kim, Y.; Kang, S. B.; Shin, J.; Kwak, M. H.; Kang, K.-Y.; Lee, Y.-H.; Park, N.; Min, B. A terahertz metamaterial with unnaturally high refractive index. Nature 2011, 470, 369-373.

(48) Shen, J. T.; Catrysse, P. B.; Fan, S. Mechanism for designing metallic metamaterials with a high index of refraction. Phys. Rev. Lett. 2005, 94, 197401.

(49) Wu, D. M.; Naik, G. V.; Solomon, M. L.; Garcia-Etxarri, A.; Salleo, A.; Dionne, J. D. Chemically responsive elastomers exhibiting positive-to-negative refractive index modulation. Nat. Nanotechnol. In review.

(50) Bohren, C. F.; Human, D. R. Absorption and Scattering of Light by Small Particles; John Wiley & Sons, 2008.

(51) Balavoine, G.; Moradpour, A.; Kagan, H. B. Preparation of chiral compounds with high optical purity by irradiation with circularly polarized light, a model reaction for the prebiotic generation of optical activity. J. Am. Chem. Soc. 1974, 96, 5152-5158.

(52) Analytical / Chromatography Products, Sigma-Aldrich, 2017

(53) Chhabra et al., IJABMR 16, 2013.

(54) Lewis et al. Nature 401, 1999.

(55) S. Ho, et al., Enhancing Enantioselective Absorption Using Dielectric Nano spheres. ACS Photonics doi: 10.102 1/acsphotonics.6b00701 (2017).

What is claimed is:

1. A method for selective photolysis of one chiral enantiomer of a compound, the method comprising:
providing a solution comprising two chiral enantiomers of the compound;
adding a nanostructure to the solution;
irradiating the solution with a circularly polarized light in the IR range of the electromagnetic spectrum; and
exposing the solution to a local electric field and a local magnetic field, such that the circularly polarized light is differentially absorbed by the one chiral enantiomer, thereby achieving the selective photolysis of the one chiral enantiomer of the compound.

2. The method of claim 1, wherein the nanostructure supports optical frequency electric resonances and optical frequency magnetic resonances.

3. The method of claim 2, wherein the nanostructure is excited with the circularly polarized light, thereby causing interference between the optical frequency electric resonances and optical frequency magnetic resonances.

4. The method of claims 3, wherein a differential absorption of the circularly polarized light by the one chiral enantiomer and a rate of differential absorption of the circularly polarized light by the one chiral enantiomer are enhanced.

5. The method of claim 4, wherein the differential absorption of the circularly polarized light by the one chiral enantiomer is enhanced about 17-fold to about 510-fold.

6. The method of claim 1, wherein a rate of differential absorption of the circularly polarized light by the one chiral enantiomer is enhanced about 2-fold to about 21-fold.

7. The method of claim 1, wherein the nanostructure is provided as an array or as a suspension.

8. The method of claim 1, wherein the nanostructure is a nanosphere, nanocylinder, nanoplate, nanoshell, nanorod, nanorice, nanofiber, nanowire, nanopyramid, nanoprism, nanostar, nanocrescent, nanoring, nanoantenna, or a combination thereof.

9. The method of claim 1, wherein a size of the nanostructure ranges from about 1 nm to about 10,000 nm.

10. A method for selective enrichment of one enantiomer a chiral compound, the method comprising:
providing a solution comprising two chiral enantiomers of the compound;
adding a nanostructure to the solution;
irradiating the solution with a circularly polarized light in the IR range of the electromagnetic spectrum; and
exposing the solution to a local electric field and a local magnetic field, such that the circularly polarized light is differentially absorbed by the one chiral enantiomer, resulting in the selective photolysis of the one chiral enantiomer of the compound, thereby achieving enrichment of one enantiomer a chiral compound.

* * * * *